US009877906B2

(12) United States Patent
Doi et al.

(10) Patent No.: US 9,877,906 B2
(45) **Date of Patent: *Jan. 30, 2018**

(54) CLEANSING COMPOSITION FOR SKIN OR HAIR

(71) Applicant: KAO CORPORATION, Tokyo (JP)

(72) Inventors: Yasuhiro Doi, Kainan (JP); Tomoko Uchiyama, Wakayama (JP)

(73) Assignee: KAO CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/417,073

(22) PCT Filed: Sep. 19, 2013

(86) PCT No.: PCT/JP2013/076172

§ 371 (c)(1),
(2) Date: Jan. 23, 2015

(87) PCT Pub. No.: WO2014/046299

PCT Pub. Date: Mar. 27, 2014

(65) Prior Publication Data

US 2015/0202133 A1 Jul. 23, 2015

(30) Foreign Application Priority Data

Sep. 20, 2012 (JP) ................................ 2012-207650
Jun. 25, 2013 (JP) ................................ 2013-133203

(51) Int. Cl.

| | |
|---|---|
| ***A61K 8/46*** | (2006.01) |
| ***A61K 8/36*** | (2006.01) |
| ***A61Q 5/02*** | (2006.01) |
| ***A61K 8/39*** | (2006.01) |
| ***A61K 8/44*** | (2006.01) |
| ***A61K 8/60*** | (2006.01) |
| ***A61Q 5/12*** | (2006.01) |
| ***A61Q 19/10*** | (2006.01) |
| ***A61K 8/37*** | (2006.01) |

(52) U.S. Cl.

CPC .............. *A61K 8/466* (2013.01); *A61K 8/361* (2013.01); *A61K 8/37* (2013.01); *A61K 8/39* (2013.01); *A61K 8/44* (2013.01); *A61K 8/463* (2013.01); *A61K 8/604* (2013.01); *A61Q 5/02* (2013.01); *A61Q 5/12* (2013.01); *A61Q 19/10* (2013.01); *A61K 2800/596* (2013.01)

(58) Field of Classification Search

None

See application file for complete search history.

(56) References Cited

U.S. PATENT DOCUMENTS

| | | | |
|---|---|---|---|
| 3,332,878 | A | 7/1967 | Coward et al. |
| 3,708,437 | A | 1/1973 | Sweeney |
| 3,808,157 | A | 4/1974 | Dewitt et al. |
| 4,028,283 | A | 6/1977 | Murata et al. |
| 4,075,129 | A | 2/1978 | Murata et al. |
| 4,220,548 | A | 9/1980 | Hashimoto et al. |
| 4,507,223 | A | 3/1985 | Tano et al. |
| 4,555,351 | A | 11/1985 | Morita et al. |
| 4,589,988 | A | 5/1986 | Rieck et al. |
| 4,597,879 | A | 7/1986 | Morita et al. |
| 4,715,991 | A | 12/1987 | Hirakouchi et al. |
| 4,852,653 | A | 8/1989 | Borchardt |
| 4,925,976 | A | 5/1990 | Terao et al. |
| 5,078,916 | A | 1/1992 | Kok et al. |
| 5,580,494 | A | 12/1996 | Sandhu et al. |
| 5,876,705 | A | 3/1999 | Uchiyama et al. |
| 6,156,297 | A | 12/2000 | Maurin et al. |
| 6,184,190 | B1 | 2/2001 | D'Ambrogio et al. |
| 6,403,654 | B1 | 6/2002 | De Oliveira |
| 6,586,379 | B1 | 7/2003 | Seipel |
| 6,656,454 | B1 | 12/2003 | Koester et al. |
| 2002/0146442 | A1 * | 10/2002 | Sendelbach .......... A61K 8/8117 424/401 |
| 2007/0031362 | A1 | 2/2007 | Kreeger et al. |
| 2011/0039744 | A1 | 2/2011 | Heath et al. |
| 2012/0058067 | A1 | 3/2012 | Van Gogh et al. |
| 2012/0270764 | A1 | 10/2012 | Brown et al. |

(Continued)

FOREIGN PATENT DOCUMENTS

| | | | |
|---|---|---|---|
| CA | 1338239 | C | 4/1996 |
| CN | 86 1 02800 | A | 1/1987 |

(Continued)

OTHER PUBLICATIONS

WikiHow, How to shampoo and condition your hair, https://web.archive.org/web/20090418054258/http://www.wikihow.com/Shampoo-and-C . . . , Apr. 18, 2009.*

Kao, Kao Akypo RLM-45NV, retrieved online on Dec. 6, 2016.*

Foster: Sulfonation and Sulfation Processes, 1997.*

Suresh et al., Revisiting Markovnikov Addition to Alkenes via Molecular Electrostatic Potential, J. Org. Chem. 2001, 66, 6883-6890.*

U.S. Office Action for U.S. Appl. No. 14/417,079, dated Jan. 25, 2016.

International Search Report and Written Opinion of the International Searching Authority dated Mar. 20, 2013, for International Application No. PCT/JP2013/076176.

(Continued)

*Primary Examiner* — Jennifer A Berrios

(74) *Attorney, Agent, or Firm* — Birch, Stewart, Kolasch & Birch, LLP

(57) ABSTRACT

There is provided a cleansing composition for skin or hair which can provide a good durability of foam and rinse feel, enhance combing property of the hair during rinsing to impart softness to the hair, and impart a refreshing feeling upon application to the skin without causing stickiness. A cleansing composition for skin or hair contains the following (A) and (B): (A) an internal olefin sulfonate having 12 or more and 24 or less carbon atoms; and (B) an anionic surfactant having no sulfate group except the internal olefin sulfonate (A) and an anionic surfactant having two or more carboxylic acid groups.

9 Claims, No Drawings

(56) References Cited

U.S. PATENT DOCUMENTS

| | | | |
|---|---|---|---|
| 2013/0252855 | A1 | 9/2013 | Weerasooriya et al. |
| 2014/0079658 | A1 | 3/2014 | Terazaki et al. |
| 2014/0080747 | A1 | 3/2014 | Hirahara et al. |
| 2015/0202134 | A1 | 7/2015 | Yoshikawa et al. |

FOREIGN PATENT DOCUMENTS

| | | | |
|---|---|---|---|
| EP | 0 377 261 | A2 | 7/1990 |
| EP | 0351928 | B1 | 6/1993 |
| JP | 49-78706 | | 7/1974 |
| JP | 54-134711 | A | 10/1979 |
| JP | 55-43138 | A | 3/1980 |
| JP | 55-56196 | A | 4/1980 |
| JP | 56-167799 | A | 12/1981 |
| JP | 59-27995 | A | 2/1984 |
| JP | 59-222466 | A | 12/1984 |
| JP | 61-134366 | A | 6/1986 |
| JP | 61-45964 | B2 | 10/1986 |
| JP | 1-151510 | A | 6/1989 |
| JP | 1-272564 | A | 10/1989 |
| JP | 2003-81935 | A | 3/2003 |
| JP | 2003-183152 | A | 7/2003 |
| JP | 2006-527785 | A | 12/2006 |
| JP | 2007-15940 | A | 1/2007 |
| JP | 2009-256211 | A | 11/2009 |

OTHER PUBLICATIONS

International Search Report and Written Opinion of the International Searching Authority dated Mar. 20, 2014, for International Application No. PCT/JP2013/076171.

International Search Report and Written Opinion of the International Searching Authority dated Mar. 20, 2014, for International Application No. PCT/JP2013/076172.

International Search Report and Written Opinion of the International Searching Authority dated Mar. 20, 2014, for International Application No. PCT/JP2013/076173.

International Search Report and Written Opinion of the International Searching Authority dated Mar. 20, 2014, for International Application No. PCT/JP2013/076174.

Kosswig et al., "Surfactants", Wiley-VCH Verlag GmbH & Co. KGaA, Weinheim, 2005, XP002554753, pp. 1-76.

* cited by examiner

CLEANSING COMPOSITION FOR SKIN OR HAIR

FIELD OF THE INVENTION

The present invention relates to a cleansing composition for skin or hair such as a shampoo and a body shampoo.

BACKGROUND OF THE INVENTION

A cleansing agent is required to have a variety of functions such as emulsifying or cleaning the components of dirt and stains such as oil. Especially, unlike an industrial cleaner, a laundry cleaner, and a house cleaner, it is considered important that a cleansing agent used for skin or hair has not only detergency and excellent foaming performance, but also a favorable durability of foam, rinse feel and a good feel after rinsing and drying. Particularly in the case of hair, good finger combability and softness of the hair during rinsing and after drying are desired, and in the case of skin, such an impression is desired that a refreshing feeling is imparted to the skin after washing with a cleansing agent.

Under the foregoing circumstances, olefin sulfonate, which is one of the anionic surfactants, is generally obtained by sulfonating olefin through reactions with a gaseous sulfur trioxide-containing gas, followed by neutralization and then hydrolysis of the resulting sulfonic acid. Olefin sulfonate is used in various cleansing agents.

For example, Patent Document 1 discloses a cleansing composition containing a specific internal olefin sulfonate for the purposes of increasing the solubilizing ability, penetrating ability, and interfacial tension reducing ability, and describes that when the above cleansing composition is used as a shampoo, it lathers well without friction, and achieves an improved feel. Also, Patent Document 2 discloses a cleansing composition containing a specific internal olefin sulfonate for the purposes of improving detergency, and describes examples of application to shampoos and the like, and Patent Document 3 also describes an aqueous liquid cleansing agent containing a specific internal olefin sulfonate and having a low cloud point.

On the other hand, Patent Document 4 discloses a cleansing composition containing an olefin sulfonate and a low-viscosity hydrophobic silicone oil such as octamethyltetrasiloxane or decamethylpentasiloxane to improve smoothness and dry touch of hair after drying. Patent Document 5 discloses a shampoo composition containing higher secondary alcohol alkoxylate sulfate having a specific structure as the composition which is low-irritant to skin or the like and can enhance detergency.

CITATION LIST

Patent Document

[Patent Document 1] JP-A-2003-81935
[Patent Document 2] U.S. Pat. No. 5,078,916
[Patent Document 3] U.S. Pat. No. 3,708,437
[Patent Document 4] JP-A-01-151510
[Patent Document 5] JP-A-2007-015940

SUMMARY OF THE INVENTION

The present invention provides a cleansing composition for skin or hair, comprising the following (A) and (B) (hereinbelow, may also be referred to as "the cleansing composition of the present invention"):

(A) an internal olefin sulfonate having 12 or more and 24 or less carbon atoms; and (B) an anionic surfactant having no sulfate group except the internal olefin sulfonate (A) and an anionic surfactant having two or more carboxylic acid groups.

Also, the present invention provides a method for washing hair, comprising applying the aforementioned cleansing composition of the present invention to hair, followed by washing and then rinsing (hereinbelow, may also be referred to as "the method for washing hair according to the present invention").

Further, the present invention provides a method for washing the body, comprising applying the aforementioned cleansing composition of the present invention to a surface of the skin, followed by washing and then rinsing (hereinbelow, may also be referred to as "the method for washing skin according to the present invention").

DETAILED DESCRIPTION OF THE INVENTION

When the cleansing agent for skin or hair contains the higher secondary alcohol alkoxylate sulfate having a specific structure, and the amount of an ether group to be introduced is small in the sulfate, the cleansing agent contains a large amount of alkyl sulfate, which cannot sufficiently reduce irritation. When the amount of the ether group to be introduced is large, lathering may be remarkably reduced. In such situation, surfactant having no sulfate group with low irritation property has been developed, which attains compatibility of low irritation property and good detergency. However, the surfactant is insufficiently satisfied as the cleansing agent for skin or hair.

Therefore, the present invention provides a cleansing composition for skin or hair which can provide a good durability of foam and rinse feel, enhance combing property of the hair after rinsing to impart softness to the hair, and impart a refreshing feeling upon application to the skin without causing stickiness.

The present inventors have extensively studied. As a result, they found that a cleansing composition which can exhibit an excellent durability of foam and rinse feel as a cleansing agent for skin or a cleansing agent for hair, while imparting good combing property and softness to the hair after rinsing, and imparting a refreshing feeling upon application to the skin after using without causing stickiness is obtained by using a specific internal olefin sulfonate and a specific anion surfactant having no sulfate group in combination.

The cleansing composition of the present invention can not only bring about a good durability of foam and quickness of rinse (hereinbelow, may also be referred to as "rinse feel"), but also, when applied to hair, impart good combing property and softness to hair during rinsing, while when applied to skin, impart a refreshing feeling to skin.

Hereinbelow, the present invention will be described in detail.

The cleansing composition of the present invention contains the following (A) and (B):

(A) an internal olefin sulfonate having 12 or more and 24 or less carbon atoms; and (B) an anionic surfactant having no sulfate group except the internal olefin sulfonate (A) and an anionic surfactant having two or more carboxylic acid groups.

The reason is not clear why the cleansing composition of the present invention can impart an excellent durability of foam and rinse feel, combing property and softness to hair during rinsing, and a refreshing feeling to the skin. The reason is estimated as follows. Because the internal olefin sulfonate having 12 or more and 24 or less carbon atoms has moderate hydrophobicity, defoaming is easily achieved in a dilution region by rinsing, to quickly rinse a surfactant component containing the component (A) and the component (B), and an oil and an active material or the like causing a friction and stickiness are removed. Thereby, combing property and softness of the hair during rinsing are improved, and a refreshing feeling of the skin is improved.

<Internal Olefin Sulfonate (A)>

From the viewpoint of environmental stability, low irritation property and the like, and from the viewpoint of improving an excellent durability of foam and rinse feel, combing property to the hair during rinsing, and a refreshing feeling to the skin, the cleansing composition of the present invention contains an internal olefin sulfonate (hereinafter, referred to as a component (A)) having 12 or more and 24 or less carbon atoms.

In the present invention, an internal olefin sulfonate is an olefin sulfonate obtained by sulfonating an internal olefin (an olefin having a double bond inside the olefin chain) as the raw material, followed by neutralization and then hydrolysis. It should be noted that the above internal olefin has a broad meaning including a trace amount of so-called α-olefin, in which a double bond is present at the C-1 position of the carbon chain. That is, sulfonation of an internal olefin quantitatively produces β-sultone, some of which are converted into γ-sultone and olefin sulfonic acid, which are further converted into hydroxyalkane sulfonate and olefin sulfonate in the process of neutralization and hydrolysis (for example, J. Am. Oil Chem. Soc. 69, 39 (1992)). Here, the hydroxyl group of the hydroxyalkane sulfonate thus obtained is present inside the alkane chain, and the double bond of the olefin sulfonate is present inside the olefin chain. Also, the product thus obtained is mainly a mixture of the aforementioned substances, which may partially contain a trace amount of hydroxyalkane sulfonate having a hydroxyl group at the end of the carbon chain or olefin sulfonate having a double bond at the end of the carbon chain. In the present specification, each of these products and a mixture thereof are collectively referred to as internal olefin sulfonate (component (A)). Also, it should be noted that hydroxyalkane sulfonate is referred to as the hydroxy form of an internal olefin sulfonate (hereinbelow, may also be referred to as HAS), and olefin sulfonate is referred to as the olefin form of an internal olefin sulfonate (hereinbelow, may also be referred to as IOS).

From the viewpoint of improving durability of foam, and imparting good combing property and softness to hair during rinsing and a refreshing feeling to the skin, the internal olefin sulfonate of the component (A) has 12 or more carbon atoms, preferably 14 or more, and more preferably 16 or more. From the viewpoint of rinse feel, combing property, softness during rinsing hair, refreshing feeling to skin, the internal olefin sulfonate of the component (A) has 24 or less carbon atoms, preferably 20 or less, and more preferably 18 or less. From the above viewpoints, the internal olefin sulfonate contained in the component (A) has 12 or more and 24 or less carbon atoms, preferably 14 or more and 20 or less, and more preferably 16 or more and 18 or less. These hydroxy form and olefin form containing various numbers of carbon atoms are derived from an internal olefin to be used as the raw material, and a hydroxy form and an olefin form containing different numbers of carbon atoms from those described above may also be contained.

From the viewpoint of improving detergency, foam quality, foamability, durability of foam and a rinse feel, and imparting good combing property and softness to hair during rinsing and a refreshing feeling to the skin, the mass content ratio of an internal olefin sulfonate having 16 carbon atoms to an internal olefin sulfonate having 18 carbon atoms (internal olefin sulfonate having 16 carbon atoms/internal olefin sulfonate having 18 carbon atoms) in the component (A) or the cleansing composition is preferably from 50/50 to 99/1, more preferably from 60/40 to 95/5, more preferably from 70/30 to 90/10, more preferably from 75/25 to 90/10, more preferably from 75/25 to 85/15, and even more preferably from 78/22 to 85/15.

It is to be noted that the aforementioned mass ratio may be measured by a high-performance liquid chromatograph-mass spectrometer (hereinbelow, abbreviated as HPLC-MS). Specifically, an internal olefin sulfonate having 16 carbon atoms and an internal olefin sulfonate having 18 carbon atoms are separated from the component (A) or the produced cleansing composition by HPLC, each of which may then be identified by analysis with MS, and from the HPLC-MS peak area of each internal olefin sulfonate, the mass ratio between them may be obtained.

From the viewpoint of improving detergency, foam quality, foamability, durability of foam, and imparting good combing property and softness to hair during rinsing and a refreshing feeling to the skin, the total content of an internal olefin sulfonate having 16 carbon atoms and an internal olefin sulfonate having 18 carbon atoms in the component (A) is preferably 50% by mass or more, more preferably 60% by mass or more, more preferably 70% by mass or more, more preferably 80% by mass or more, more preferably 90% by mass or more, and even more preferably 95% by mass or more. It should be noted that the upper limit of the aforementioned total content is 100% by mass.

As is apparent from the aforementioned production method, the sulfonate group of the internal olefin sulfonate of the component (A) is present in the carbon chain of an internal olefin sulfonate, namely inside the olefin chain or alkane chain, and the component (A) may partially contain a trace amount of an internal olefin sulfonate having a sulfonate group at the end of the carbon chain. In the present invention, from the viewpoint of foamability, it is preferable that the content of an internal olefin sulfonate in which the sulfonate group is present at the C-2 position of the carbon chain is low, while the content of an internal olefin sulfonate in which the sulfonate group is present further inside is high in the component (A). It should be noted that when the component (A) contains an internal olefin sulfonate having 16 carbon atoms and an internal olefin sulfonate having 18 carbon atoms, it is more preferable that the content of an internal olefin sulfonate in which the sulfonate group is present at the C-2 position of the carbon chain is low, with respect to both of the above internal olefin sulfonates having 16 and 18 carbon atoms.

From the viewpoint of improving lathering property, foam quality, and a rinse feel as well as imparting good combing property and softness to hair during rinsing, the content of an internal olefin sulfonate in which the sulfonate group is present at the C-2 position in the component (A) is preferably 25% by mass or less, more preferably 24% by mass or less, more preferably 23% by mass or less, more preferably 22% by mass or less, preferably 20% by mass or less, more preferably less than 20% by mass, more preferably 19% by mass or less, and even more preferably 18% by mass or less. Also, from the viewpoint of rinse feel and combing property during rinsing hair, the content of an internal olefin sulfonate in which the sulfonate group is present at the C-2 position in the component (A) is preferably 17.5% by mass or less, more preferably 15% by mass or less, more preferably 12% by mass or less, and even more preferably 10% by mass or less. Also, from the viewpoint of reducing the production cost and improving productivity, and from the viewpoint of durability of foam, softness during rinsing hair and a refreshing feeling to the skin, the lower limit of the content of an internal olefin sulfonate in which the sulfonate group is present at the C-2 position in the component (A) is preferably 5% by mass or more, more preferably 6% by mass or more, more preferably 7% by mass or more, and even more preferably 8% by mass or more. Also, from the viewpoint of durability of foam, refreshing feeling to the skin, the lower limit of the content of an internal olefin sulfonate in which the sulfonate group is present at the C-2 position in the component (A) is preferably 9% by mass or more, more preferably 10% by mass or more, more preferably 12% by mass or more, more preferably 14% by mass or more, and even more preferably 16% by mass or more. Further, from the above viewpoints, the content of an internal olefin sulfonate in which the sulfonate group is present at the C-2 position in the component (A) is preferably 5% by mass or more and 25% by mass or less, more preferably 5% by mass or more and 24% by mass or less, more preferably 5% by mass or more and 23% by mass or less, more preferably 5% by mass or more and 22% by mass or less, preferably 5% by mass or more and 20% by mass or less, more preferably 6% by mass or more and less than 20% by mass, more preferably 7% by mass or more and 19% by mass or less, more preferably 8% by mass or more and 18% by mass or less, and even more preferably 9% by mass or more and 17.5% by mass or less.

Also, from the viewpoint of rinse feel and combing property during rinsing hair, the content of an internal olefin sulfonate in which the sulfonate group is present at the C-2 position in the component (A) is preferably 9% by mass or more and 17.5% by mass or less, more preferably 9% by mass or more and 15% by mass or less, more preferably 9% by mass or more and 12% by mass or less, and even more preferably 9% by mass or more and 10% by mass or less. Also, from the viewpoint of durability of foam, refreshing feeling to the skin, the content of an internal olefin sulfonate in which the sulfonate group is present at the C-2 position in the component (A) is preferably 9% by mass or more and 18% by mass or less, more preferably 10% by mass or more and 18% by mass or less, more preferably 12% by mass or more and 18% by mass or less, more preferably 14% by mass or more and 18% by mass or less, and even more preferably 16% by mass or more and 18% by mass or less.

It should note that the content of an internal olefin sulfonate in which the sulfonate group is present at the C-2 position in the component (A) may be measured by a method such as nuclear magnetic resonance spectroscopy. More specifically, it may be measured by a method using gas chromatography described later in Example.

Also, from the viewpoint of improving lathering property, foam quality, durability of foam and rinse feel as well as imparting good combing property and softness to hair during rinsing and a refreshing feeling to skin, the content of an olefin sulfonate in which the sulfonate group is present at the C-1 position of the olefin chain or alkane chain in the component (A) is preferably 3.0% by mass or less, more preferably 2.5% by mass or less, more preferably 2.0% by mass or less, more preferably 1.5% by mass or less, and even more preferably 1.0% by mass or less. From the viewpoint of reducing the production cost and improving productivity, the lower limit of the aforementioned content is preferably 0.01% by mass or more.

Further, from the viewpoint of improving lathering property, foam quality, durability of foam and rinse feel as well as imparting good combing property and softness to hair during rinsing and a refreshing feeling to skin, the content of an internal olefin sulfonate in which the sulfonate group is present further inside than the C-3 position of the olefin chain or alkane chain in the component (A) is preferably 70% by mass or more, more preferably 75% by mass or more, and even more preferably 80% by mass or more.

The internal olefin sulfonate is preferably a mixture of the hydroxy form and the olefin form. From the viewpoint of improving productivity and reducing impurities, the mass content ratio (hydroxy form/olefin form) of the hydroxy form of an internal olefin sulfonate to the olefin form of an internal olefin sulfonate in the component (A) or the cleansing composition is preferably from 50/50 to 100/0, more preferably from 60/40 to 100/0, more preferably from 70/30 to 100/0, more preferably from 75/25 to 100/0, and even more preferably from 75/25 to 95/5.

The mass content ratio of the hydroxy form of an internal olefin sulfonate to the olefin form of an internal olefin sulfonate in the component (A) or the cleansing composition according to the present invention may be obtained by separating the hydroxy form and the olefin form from the component (A) or the produced cleansing composition by HPLC and then measuring the separated substances by the method described in Examples.

From the viewpoint of improving a durability of foam and rinse feel as well as imparting good combing property and softness to hair, and a refreshing feeling to skin, the content of the aforementioned component (A) in the cleansing composition of the present invention is preferably 0.1% by mass or more, more preferably 1% by mass or more, more preferably 2% by mass or more, more preferably 3% by mass or more, and even more preferably 5% by mass or more. Also, from the viewpoint of improving durability of foam and rinse feel, and combing property and softness to hair and a refreshing feeling to the skin, the content of the aforementioned component (A) in the cleansing composition of the present invention is preferably 80% by mass or less, more preferably 50% by mass or less, more preferably 30% by mass or less, more preferably 20% by mass or less, more preferably 10% by mass or less, and even more preferably 8% by mass or less. Also, from the above viewpoints, the content of the aforementioned component (A) in the cleansing composition of the present invention is preferably 0.1% by mass or more and 80% by mass or less, more preferably 1% by mass or more and 50% by mass or less, more preferably 2% by mass or more and 30% by mass or less, more preferably 3% by mass or more and 20% by mass or less, more preferably 3% by mass or more and 10% by mass or less, and even more preferably 5% by mass or more and 8% by mass or less.

The internal olefin sulfonate (A) is obtainable by sulfonating an internal olefin having 12 or more and 24 or less carbon atoms, followed by neutralization and then hydrolysis. No particular limitation is imposed on the conditions of sulfonation, neutralization, and hydrolysis, and for example, the conditions described in U.S. Pat. Nos. 1,633,184 and 2,625,150, and Tenside Surf. Det. 31 (5) 299 (1994) may be referred to.

As mentioned above, in the present invention, a raw material internal olefin refers to an olefin having a double bond inside the olefin chain. From the viewpoint of improving the lathering property, durability of foam and rinse feel of the obtained cleansing composition, and combing property and softness of the hair during rinsing, and imparting a refreshing feeling to skin, the number of carbon atoms in the raw material internal olefin is preferably from 12 to 24, more preferably from 12 to 20, more preferably from 12 to 18, more preferably from 14 to 18, and even more preferably from 16 to 18. An internal olefin to be used may be used singly or a combination of two or more thereof may be used.

From the viewpoint of acquiring lathering property and a creamy foam quality for easy washing, improving a rinse feel, imparting good combing property and softness to hair during rinsing, the content of an internal olefin in which the double bond is present at the C-2 position in the raw material internal olefin is preferably 40% by mass or less, more preferably 35% by mass or less, more preferably 32% by mass or less, more preferably 30% by mass or less, and even more preferably 27% by mass or less, and also, from the viewpoint of rinse feel and combing property of hair, more preferably 25% by mass or less, more preferably 20% by mass or less, more preferably less than 20% by mass, more preferably 19% by mass or less, and even more preferably 18% by mass or less. Also, from the viewpoint of reducing the production cost, improving productivity, and durability of foam, softness during rinsing hair and a refreshing feeling to the skin, the lower limit of the aforementioned content is preferably 5% by mass or more, more preferably 6% by mass or more, more preferably 7% by mass or more, more preferably 8% by mass or more, more preferably 9% by mass or more, more preferably 12% by mass or more, and even more preferably 15% by mass or more, and also from the viewpoint of durability of foam, and refreshing feeling to the skin, more preferably 20% by mass or more, more preferably 22% by mass or more, and even more preferably 24% by mass or more. Also, from the above viewpoints, it is preferably 5% by mass or more and 40% by mass or less, more preferably 5% by mass or more and 35% by mass or less, more preferably 5% by mass or more and 32% by mass or less, more preferably 5% by mass or more and 30% by mass or less, preferably 6% by mass or more and 30% by mass or less, more preferably 7% by mass or more and 30% by mass or less, more preferably 8% by mass or more and 30% by mass or less, more preferably 9% by mass or more and 30% by mass or less, more preferably 12% by mass or more and 30% by mass or less, and even more preferably 15% by mass or more and 27% by mass or less.

Further, from the viewpoint of rinse feel and combing property of hair, the content of an internal olefin in which the double bond is present at the C-2 position in the raw material internal olefin is preferably 15% by mass or more and 25% by mass or less, more preferably 15% by mass or more and 20% by mass or less, more preferably 15% by mass or more and less than 20% by mass, more preferably 15% by mass or more and 19% by mass or less, and even more preferably 15% by mass or more and 18% by mass or less. Also, from the viewpoint of durability of foam, and refreshing feeling to the skin, the content of an internal olefin in which the double bond is present at the C-2 position in the raw material internal olefin is preferably 20% by mass or more and 27% by mass or less, more preferably 22% by mass or more and 27% by mass or less, and even more preferably 24% by mass or more and 27% by mass or less.

Also, from the viewpoint of improving lathering property, foam quality, durability of foam and rinse feel as well as imparting good combing property and softness to hair during rinsing and a refreshing feeling to skin, the content of an olefin in which the double bond is present at the C-1 position, namely α-olefin, in the raw material internal olefin is preferably 3.0% by mass or less, more preferably 2.5% by mass or less, more preferably 2.0% by mass or less, more preferably 1.5% by mass or less, and even more preferably 1.0% by mass or less. From the viewpoint of reducing the production cost and improving productivity, the lower limit of the aforementioned content is preferably 0.01% by mass or more.

Further, from the viewpoint of improving lathering property, foam quality, durability of foam and rinse feel as well as imparting good combing property and softness to hair during rinsing and a refreshing feeling to skin, the total content of a raw material internal olefin in which the double bond is present further inside than the C-3 position in the raw material internal olefin is preferably 65% by mass or more, more preferably 70% by mass or more, more preferably 75% by mass or more, and even more preferably 80% by mass or more.

The distribution of the double bond in the raw material internal olefin may be measured by a method described in Examples using a gas chromatograph mass spectrometer (hereinbelow, abbreviated as GC-MS). Specifically, components each having different carbon chain lengths and double bond positions are accurately separated by a gas chromatograph analyzer (hereinbelow, abbreviated as GC), and each component is then analyzed by a mass spectrometer (hereinbelow, abbreviated as MS) to identify the position of double bond in it, and from the resulting GC peak area, the fraction of each component may be found out.

The sulfonation reaction may be carried out by reacting a sulfur trioxide gas with an internal olefin at a ratio of from 1.0 to 1.2 moles of sulfur trioxide per mole of raw material internal olefin. The reactions can be carried out at a reaction temperature of from 20 to 40° C.

Neutralization is carried out by reacting from 1.0 to 1.5 times the molar amount of an alkaline aqueous solution such as sodium hydroxide, ammonia, or 2-aminoethanol with the theoretical value of sulfonate group.

The hydrolysis reaction may be carried out at from 90 to 200° C. for from 30 minutes to three hours in the presence of water. These reactions may be successively carried out. Also, upon completion of the reactions, the products may be purified by extraction, washing, and the like.

Also, in the production of the internal olefin sulfonate (A), the raw material internal olefin in which the number of carbon atoms is distributed in from 12 to 24 may be subjected to sulfonation, neutralization, and hydrolysis, or the raw material internal olefin having a uniform number of carbon atoms may be subjected to sulfonation, neutralization, and hydrolysis. Also, a plurality of internal olefin sulfonates each having different numbers of carbon atoms may be produced in advance and then mixed, as needed.

As the internal olefin sulfonate composition (A) of the present invention is obtained by sulfonating an internal olefin, followed by neutralization and hydrolysis as described above, an unreacted raw material internal olefin and inorganic compounds may remain in the composition (A). It is preferred that the contents of these components are much smaller.

The content of the raw material internal olefin in the component (A) of the present invention is preferably less than 5.0% by mass, more preferably less than 3.0% by mass, more preferably less than 1.5% by mass, and even more preferably less than 1.0% by mass in the component (A), from the viewpoint of improving durability of foam and rinse feel, and imparting to hair good combing property and softness during rinsing and imparting refreshing feeling to skin.

The content of the unreacted internal olefin may be measured by a method described later in Examples.

The content of the inorganic compounds in the component (A) of the present invention is preferably less than 7.5% by mass, more preferably less than 5.0% by mass, more preferably less than 3.0% by mass, more preferably less than 2.0% by mass, and even more preferably less than 1.6% by mass in the component (A), from the viewpoint of improving durability of foam and rinse feel, and imparting to hair good combing property and softness during rinsing and imparting refreshing feeling to skin.

In this context, the inorganic compounds include sulfates and alkali agents. The content of these inorganic compounds may be measured by a potentiometric titration. Specifically, the content may be measured by a method described later in Examples.

<An Anionic Surfactant (B) Having No Sulfate Group Except a Component (A) and an Anionic Surfactant Having Two or More Carboxylic Acid Groups>

From the viewpoint of improving a durability of foam and rinse feel, and imparting combing property and softness to the hair, and a refreshing feeling to the skin, and from the viewpoint of reducing an irritation to the skin, the cleansing composition of the present invention contains an anionic surfactant (hereinafter, referred to as a component (B)) having no sulfate group except the component (A) and an anionic surfactant having two or more carboxylic acid groups. Herein, although the low irritation is improved when an anionic surfactant having two or more carboxylic acid groups such as an N-acyl glutamic acid salt is used as the component (B), lathering property, a rinse feel, and a refreshing feeling after rinsing are impaired. Therefore, such anionic surfactant is excluded.

From the viewpoint of improving a durability of foam and rinse feel, and imparting combing property and softness to the hair, and a refreshing feeling to the skin, and from the viewpoint of reducing an irritation to skin, the component (B) is preferably an anionic surfactant having one carboxylic acid group or an anionic surfactant having a sulfonic acid group.

Preferred specific examples of the component (B) include a fatty acid, an alkyl ether acetic acid of Formula (I), alkylsarcosine, alkylglycine, alkylalanine, sulfosuccinic acid, α-olefinsulfonic acid, secondary alkane sulfonate, linear alkylbenzene sulfonic acid, alkylisethionate, alkyl sulfo acetic acid, and salts thereof. Of these, from the viewpoint of compatibility between lathering and low irritation, as well as from the viewpoint of improving a durability of foam and rinse feel, and imparting combing property and softness to the hair, and a refreshing feeling to the skin, the secondary alkane sulfonate, the alkylisethionate, the alkyl sulfo acetic acid, the fatty acid, the alkyl ether acetic acid of formula (I), the alkylsarcosine, the sulfosuccinic acid, and the salts thereof are preferred, and an anionic surfactant represented by any of Formulae (I) to (VI) is more preferred.

$$R^1—O—(CH_2CH_2O)n^1—CH_2—COOM \quad (I)$$

(wherein $R^1$ represents an alkyl group having 4 or more and 22 or less carbon atoms; $n^1$ represents a number of 4.0 or more and 16 or less; and M represents a hydrogen atom, an alkali metal, an alkaline earth metal (½ atom), ammonium, or organic ammonium.)

In Formula (I), from the viewpoint of enhancing a durability of foam and rinse feel, and improving combing property of the hair during rinsing when the cleansing composition of the present invention is applied to the hair, and imparting softness to the hair, and from the viewpoint of imparting a refreshing feeling to the skin when the cleansing composition of the present invention is applied to a body, $R^1$ is an alkyl group having 4 or more and 22 or less carbon atoms, preferably 8 or more and 18 or less, more preferably 10 or more and 16 or less, and even more preferably 12 or more and 14 or less. In Formula (I), from the viewpoint of improving a durability of foam and rinse feel, and imparting combing property and softness to the hair, and a refreshing feeling to the skin, and from the viewpoint of foamability and low irritation of the cleansing composition, $n^1$ is an average mole number of an ethyleneoxy group added, and is 4 or more and 16 or less, preferably 4 or more and 10 or less, more preferably 4.5 or more and 10 or less, and even more preferably 4.5 or more and 6 or less. In Formula (I), from the viewpoint of improving a durability of foam and rinse feel, and imparting combing property and softness to the hair, and a refreshing feeling to the skin, and from the viewpoint of improving water solubility, M is a hydrogen atom, an alkali metal, an alkaline earth metal (½ atom), ammonium, or organic ammonium, preferably the hydrogen atom, the alkali metal, the ammonium, or the organic ammonium, more preferably the alkali metal, the ammonium, or the organic ammonium, more preferably the alkali metal, and even more preferably sodium or potassium.

Examples of the compound represented by Formula (I) include sodium polyoxyethylene (4.5) lauryl ether acetate, potassium polyoxyethylene (4.5) lauryl ether acetate, or sodium polyoxyethylene (10) lauryl ether acetate. Specific examples of the commercially available compound include "BEAULIGHT" manufactured by Sanyo Chemical Industries, Ltd., "KAO AKYPO RLM" series manufactured by Kao Corporation, and "Miracare" series manufactured by Solvay-Rhodia.

(II)

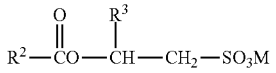

(wherein $R^2$ represents an alkyl group having 4 or more and 22 or less carbon atoms; $R^3$ represents a hydrogen atom or an alkyl group having from 1 to 4 carbon atoms; and M represents a hydrogen atom, an alkali metal, an alkaline earth metal (½ atom), ammonium, or organic ammonium.)

In Formula (II), from the viewpoint of enhancing a durability of foam and rinse feel, improving combing property of the hair during rinsing when the cleansing composition of the present invention is applied to the hair, and imparting softness to the hair, and from the viewpoint of imparting a refreshing feeling to the skin when the cleansing composition of the present invention is applied to the body, $R^2$ is an alkyl group having 4 or more and 22 or less carbon atoms, preferably 8 or more and 18 or less, more preferably 10 or more and 16 or less, and even more preferably 12 or more and 14 or less. $R^3$ represents a hydrogen atom or an alkyl group having from 1 to 4 carbon atoms. From the viewpoint of lathering property, $R^3$ is preferably a hydrogen atom or a methyl group, and more preferably the hydrogen atom. In Formula (II), from the viewpoint of enhancing a durability of foam and rinse feel, improving combing property of the hair during rinsing when the cleansing composition of the present invention is applied to the hair, and imparting the softness to the hair, from the viewpoint of imparting a refreshing feeling to the skin when the cleansing composition of the present invention is applied to the body, and from the viewpoint of improving water solubility, M is a hydrogen atom, an alkali metal, an alkaline earth metal (½ atom), ammonium, or organic ammonium, preferably the hydrogen atom, the alkali metal, the ammonium, or the organic ammonium, more preferably the alkali metal, the ammonium, or the organic ammonium, more preferably the alkali metal, and even more preferably sodium or potassium.

Examples of the compound represented by Formula (II) include ammonium cocoyl isethionate, sodium lauroyl isethionate, sodium lauroyl methyl isethionate, or sodium cocoyl methyl isethionate. Specific examples of the commercially available compound include "Iselux LQ-CLR" manufactured by Innospec Inc., "Diapon CI" series manufactured by NOF CORPORATION, "Hostapon STCI" series manufactured by Clariant Corporation, and "Jordapon CI" series manufactured by BASF Corporation.

(III)

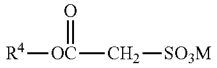

(wherein $R^4$ represents an alkyl group having 4 or more and 22 or less carbon atoms, and M represents a hydrogen atom, an alkali metal, an alkaline earth metal (½ atom), ammonium, or organic ammonium.)

In Formula (III), from the viewpoint of enhancing a durability of foam and rinse feel, improving combing property of the hair during rinsing when the cleansing composition of the present invention is applied to the hair, and imparting softness to the hair, and from the viewpoint of imparting a refreshing feeling to the skin when the cleansing composition of the present invention is applied to the body, $R^4$ is an alkyl group having 4 or more and 22 or less carbon atoms, preferably 8 or more and 18 or less, more preferably 10 or more and 16 or less, and even more preferably 12 or more and 14 or less. In Formula (III), from the viewpoint of enhancing a durability of foam and rinse feel, improving combing property of the hair during rinsing when the cleansing composition of the present invention is applied to the hair, and imparting softness to the hair, from the viewpoint of imparting a refreshing feeling to the skin when the cleansing composition of the present invention is applied to the body, and from the viewpoint of improving water solubility, M is a hydrogen atom, an alkali metal, an alkaline earth metal (½ atom), ammonium, or organic ammonium, preferably the hydrogen atom, the alkali metal, the ammonium, or the organic ammonium, more preferably the alkali metal, the ammonium, or the organic ammonium, more preferably the alkali metal, and even more preferably sodium or potassium.

Examples of the compound represented by Formula (III) include sodium coco sulfoacetate or sodium lauryl sulfoacetate. Specific examples of the commercially available compound include "NIKKOL LSA-F" manufactured by Nikko Chemicals, Inc., and "Lathanol LAL" manufactured by Stepan Company.

(IV)

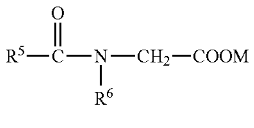

(wherein $R^5$ represents an alkyl group having 8 or more and 22 or less carbon atoms; $R^6$ represents a hydrogen atom or an alkyl group having from 1 to 4 carbon atoms; and M represents a hydrogen atom, an alkali metal, an alkaline earth metal (½ atom), ammonium, or organic ammonium.)

In Formula (IV), from the viewpoint of enhancing a durability of foam and rinse feel, improving combing property of the hair during rinsing when the cleansing composition of the present invention is applied to the hair, and imparting the softness to the hair, and from the viewpoint of imparting a refreshing feeling to the skin when the cleansing composition of the present invention is applied to the body, $R^5$ is an alkyl group having 8 or more and 22 or less carbon atoms, preferably 8 or more and 18 or less, more preferably 10 or more and 16 or less, and even more preferably 12 or more and 14 or less. $R^6$ represents a hydrogen atom or an alkyl group having from 1 to 4 carbon atoms. From the viewpoint of detergency and water solubility, $R^6$ is preferably a hydrogen atom or a methyl group, and more preferably the hydrogen atom. In Formula (IV), from the viewpoint of enhancing a durability of foam and rinse feel, improving combing property of the hair during rinsing when the cleansing composition of the present invention is applied to the hair, and imparting softness to the hair, from the viewpoint of imparting a refreshing feeling to the skin when the cleansing composition of the present invention is applied to the body, and from the viewpoint of improving water solubility, M is a hydrogen atom, an alkali metal, an alkaline earth metal (½ atom), ammonium, or organic ammonium, preferably the hydrogen atom, the alkali metal, the ammonium, or the organic ammonium, more preferably the alkali metal, the ammonium, or the organic ammonium, more preferably the alkali metal, and even more preferably sodium or potassium.

Examples of the compound represented by Formula (IV) include potassium cocoyl sarcosinate, sodium cocoyl sarcosinate, triethanolamine cocoyl sarcosinate, sodium lauroylsarcosinate, or sodium palmitoyl sarcosinate. Specific examples of the commercially available compound include sarcosinate series such as "NIKKOL SARCOSINATE CN-30", "CT-30", and "PN" manufactured by Nikko Chemicals, Inc., Soypon series such as "Soypon SC", "Soypon SCTA", "SLE", and "SLP" manufactured by Kawaken Fine Chemicals Co. Ltd., "Fillet C" manufactured by NOF CORPORATION, and "CRODASINIC LS30" manufactured by Croda International Plc.

(V)

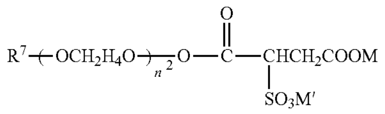

(wherein $R^7$ represents an alkyl group having 8 or more and 22 or less carbon atoms; $n^2$ represents a number of 0 or more and 3 or less; and M and M' each independently represent a hydrogen atom, an alkali metal, an alkaline earth metal (½ atom), ammonium, or organic ammonium.)

In Formula (V), from the viewpoint of enhancing a durability of foam and rinse feel, improving combing property of the hair during rinsing when the cleansing composition of the present invention is applied to the hair, and imparting softness to the hair, and from the viewpoint of imparting a refreshing feeling to the skin when the cleansing composition of the present invention is applied to the body, $R^7$ is an alkyl group having 8 or more and 22 or less carbon atoms, preferably 8 or more and 18 or less, more preferably 10 or more and 16 or less, and even more preferably 12 or more and 14 or less. In Formula (V), from the viewpoint of enhancing a durability of foam and rinse feel, improving combing property of the hair during rinsing when the cleansing composition of the present invention is applied to the hair, and imparting the softness to the hair, from the viewpoint of imparting a refreshing feeling to the skin when the cleansing composition of the present invention is applied to the body, and from the viewpoint of improving water solubility, M and M' each are independently a hydrogen atom, an alkali metal, an alkaline earth metal (½ atom), ammonium, or organic ammonium, preferably the hydrogen atom, the alkali metal, the ammonium, or the organic ammonium, more preferably the alkali metal, the ammonium, or the organic ammonium, more preferably the alkali metal, and even more preferably sodium or potassium.

Examples of the compound represented by Formula (V) include disodium lauryl sulfosuccinate, disodium laureth sulfosuccinate, or magnesium laureth sulfosuccinate. Specific examples of the commercially available compound include "REWOPOL SBFA30B" manufactured by Evonik Goldschmidt GmbH, "RIKAMILD ES-100" manufactured by New Japan Chemical Co., Ltd., and Kohacool series such as "Kohacool L-300" manufactured by TOHO Chemical Industry Co., Ltd.

$$R^8\text{—COOM} \qquad (VI)$$

(wherein $R^8$ represents an alkyl group having 8 or more and 22 or less carbon atoms; M represents a hydrogen atom, an alkali metal, an alkaline earth metal (½ atom), ammonium, or organic ammonium.)

In Formula (VI), from the viewpoint of enhancing a durability of foam and rinse feel, improving combing property of the hair during rinsing when the cleansing composition of the present invention is applied to the hair, and imparting the softness to the hair, and from the viewpoint of imparting a refreshing feeling to the skin when the cleansing composition of the present invention is applied to the body, $R^8$ is an alkyl group having 8 or more and 22 or less carbon atoms, preferably 8 or more and 20 or less, more preferably 10 or more and 18 or less, and even more preferably 12 or more and 16 or less. In Formula (VI), from the viewpoint of enhancing a durability of foam and rinse feel, improving combing property of the hair during rinsing when the cleansing composition of the present invention is applied to the hair, and imparting softness to the hair, from the viewpoint of imparting a refreshing feeling to the skin when the cleansing composition of the present invention is applied to the body, and from the viewpoint of improving water solubility, M is a hydrogen atom, an alkali metal, an alkaline earth metal (½ atom), ammonium, or organic ammonium, preferably the hydrogen atom, the alkali metal, the ammonium, or the organic ammonium, more preferably the alkali metal, the ammonium, or the organic ammonium, more preferably the alkali metal, and even more preferably sodium or potassium.

Examples of the compound represented by Formula (VI) include coconut oil fatty acid sodium, sodium laurate, sodium myristate, sodium palmitate, sodium stearate, or potassium laurate. Specific examples of the commercially available compound include "LUNAC" series and "PRIOLY B-100" manufactured by Kao Corporation, and "NAA-122" manufactured by NOF CORPORATION.

From the viewpoint of low irritation, from the viewpoint of durability of foam, from the viewpoint of improving combing property of the hair during rinsing when the cleansing composition of the present invention is applied to the hair, and imparting the softness to the hair, and from the viewpoint of imparting a refreshing feeling to the skin when the cleansing composition of the present invention is applied to the body, the content of the component (B) is preferably 0.01% by mass or more in the cleansing composition of the present invention, more preferably 0.05% by mass or more, more preferably 0.5% by mass or more, more preferably 2% by mass or more, and even more preferably 4% by mass or more. From the viewpoint of improving a durability of foam and rinse feel by the cleansing composition for skin or hair of the present invention, softness to hair during rinsing, and imparting a refreshing feeling to the skin, the content is preferably 30% by mass or less, more preferably 20% by mass or less, more preferably 15% by mass or less, more preferably 10% by mass or less, and even more preferably 8% by mass or less. From the above viewpoints, it is preferably from 0.01 to 30% by mass, more preferably from 0.05 to 20% by mass, more preferably from 0.5 to 15% by mass, more preferably from 2 to 10% by mass, and even more preferably from 4 to 8% by mass.

From the viewpoint of improving durability of foam and rinse feel, improving combing property of the hair during rinsing when the cleansing composition of the present invention is applied to the hair, and imparting the softness to the hair, and from the viewpoint of imparting a refreshing feeling to the skin when the cleansing composition of the present invention is applied to the body, the mass content ratio of the component (A) to the component (B) [component (A)/component (B)] is preferably from 0.01 to 100, more preferably from 0.05 to 20, more preferably from 0.1 to 10, more preferably from 0.2 to 6, more preferably from 0.3 to 6, and even more preferably from 0.5 to 6.

The cleansing composition of the present invention may contain a surfactant (hereinafter, referred to as a component (C)) other than the component (A) and the component (B), as far as the effect of the present invention is not impaired.

As to the surfactant other than the component (A) and the component (B), any surfactant may be used if it is usually used in medicinal products, quasi drugs, cosmetic materials, toiletries, and general merchandises or the like. Specific examples thereof include anionic surfactants, non-ionic surfactants, ampholytic surfactants, and cationic surfactants other than the component (A) and the component (B). Of these, from the viewpoint of improving detergency, foamability, and foam quality, the surfactants other than the component (A) and the component (B) are preferably anionic surfactants, non-ionic surfactants, or ampholytic surfactants other than the component (A) and the component (B).

From the viewpoint of lathering property or detergency, examples of the anionic surfactants other than the component (A) and the component (B) include ester sulfates such as alkyl sulfate, alkenyl sulfate, polyoxyalkylene alkyl ether sulfate, polyoxyalkylene alkenyl ether sulfate, and polyoxyalkylene alkylphenyl ether sulfate; ester phosphates such as alkyl phosphate and polyoxyalkylene alkyl ether phosphate; and amino acid salts such as an acyl glutamic acid salt, an alanine derivative, a glycine derivative, and an arginine derivative. From the viewpoint of further improving low irritation, the ester phosphates or the amino acid salts are preferred, and the amino acid salts are more preferred.

From the viewpoint of detergency, foamability, and foam quality, from the viewpoint of durability of foam and rinse feel, as well as from the viewpoint of imparting combing property and softness to the hair when the cleansing composition of the present invention is applied to the hair, and from the viewpoint of imparting a refreshing feeling to the skin when the cleansing composition of the present invention is applied to the body, the anionic surfactants other than the component (A) and the component (B) preferably have an alkyl group or an alkenyl group having from 8 to 18 carbon atoms, and more preferably an alkyl group or an alkenyl group having from 10 to 16 carbon atoms.

From the viewpoint of further enhancing low irritation, it is preferable to reduce the content of the anionic surfactant containing the sulfate group such as the ester sulfate among the anionic surfactants other than the component (A) and the component (B). From the viewpoint of improving-low irritation while securing good detergency, foamability, and foam quality, the content of the anionic surfactant containing the sulfate group is preferably 10% by mass or less in the cleansing composition of the present invention, more preferably 3.0% by mass or less, and even more preferably 0.5% by mass or less. It is preferred that the cleansing composition contains no anionic surfactant containing the sulfate group except for a case where the anionic surfactant is inevitably mixed.

Examples of the aforementioned nonionic surfactant include a polyethylene glycol type nonionic surfactant such as polyoxyethylene sorbitan fatty acid ester, polyoxyethylene sorbitol fatty acid ester, polyoxyethylene glycerin fatty acid ester, polyoxyethylene fatty acid ester, polyoxyethylene alkyl ether, polyoxyethylene alkyl phenyl ether, and polyoxyalkylene (hydrogenated) castor oil, a polyhydric alcohol type nonionic surfactant such as sucrose fatty acid ester, polyglycerin alkyl ether, polyglycerin fatty acid ester, and alkyl glycoside, and fatty acid alkanolamide.

Examples of the aforementioned amphoteric surfactant include a betaine surfactant such as imidazoline betaine, alkyldimethylaminoacetate betaine, fatty acid amidopropyl betaine, and sulfobetaine, and an amine oxide surfactant such as alkyl dimethyl amine oxide.

Of these, from the viewpoint of detergency, a volume of foam during cleansing, and foam quality of the cleansing composition of the present invention, from the viewpoint of imparting combing property and softness to the hair when the cleansing composition of the present invention is applied to the hair, and from the viewpoint of imparting a refreshing feeling to the skin when the cleansing composition of the present invention is applied to the body, imidazoline betaine, sulfobetaine, and fatty acid amide propyl betaine or the like are preferred. Specifically, coconut oil fatty acid amidopropyl betaine, lauryl carbomethoxy methyl hydroxyimidazolium betaine, dimethylaminoacetic acid betaine, or lauryl hydroxysulfobetaine is more preferred.

Examples of the aforementioned cationic surfactant include a mineral acid or organic acid salt of the tertiary amine represented by following Formula (1) and a quaternary ammonium salt-type surfactant represented by following Formula (2).

(1)

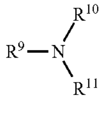

(wherein, $R^9$ represents a linear or branched alkyl group or alkenyl group having from 6 to 28 carbon atoms which may be interrupted by an amide group, an ester group, or an ether group; $R^{10}$ represents a linear or branched alkyl group, alkenyl group, or alkanol group having from 1 to 28 carbon atoms which may be interrupted by an amide group, an ester group, or an ether group; and $R^{11}$ represents a linear or branched alkyl group or alkanol group having from 1 to 3 carbon atoms.)

In the general formula (1), from the viewpoint of improving durability of foam and rinse feel, imparting to hair combing property, softness and imparting refreshing feeling to skin, and reducing irritation property to skin, the number of carbon atoms in $R^9$ is preferably from 12 to 28, more preferably from 14 to 25, and even more preferably from 16 to 25. From the similar viewpoints, the number of carbon atoms in $R^{10}$ is preferably from 12 to 28, more preferably from 14 to 25, and even more preferably from 16 to 25, or $R^{10}$ is preferably a methyl group, an ethyl group, or a hydroxyethyl group. From the similar viewpoints, $R^{11}$ is preferably a methyl group, an ethyl group, or a hydroxyethyl group.

No particular limitation is imposed on the mineral acid or organic acid which forms a salt with the tertiary amine represented by Formula (1); from the viewpoint of dispersion stability of a surfactant, hydrogen halide, sulfuric acid, acetic acid, citric acid, lactic acid, glutamic acid, and alkyl sulfate having from 1 to 3 carbon atoms are preferable, and from the viewpoint of chemical stability, hydrogen halide is preferably hydrogen chloride.

(2)

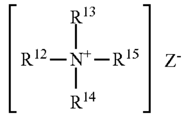

(wherein, $R^{12}$ represents a linear or branched alkyl group or alkenyl group having from 6 to 28 carbon atoms which may be interrupted by an amide group, an ester group, or an ether group; $R^{13}$ represents a linear or branched alkyl group, alkenyl group, or alkanol group having from 1 to 28 carbon atoms which may be interrupted by an amide group, an ester group, or an ether group; $R^{14}$ and $R^{15}$ each represent a linear or branched alkyl group having from 1 to 3 carbon atoms; and $Z^-$ represents an anionic group, which is the counter ion of an ammonium salt.)

In Formula (2), from the viewpoint of improving durability of foam and rinse feel, from the viewpoint of imparting combing property and softness to the hair when the cleansing composition of the present invention is applied to the hair and from the viewpoint of imparting a refreshing feeling to the skin when the cleansing composition of the present invention is applied to the body, a preferred embodiment of $R^{12}$ is the same as a preferred embodiment of $R^9$ in Formula (1). From a similar viewpoint, a preferred embodiment of $R^{19}$ is the same as a preferred embodiment of $R^{10}$ in Formula (1). Also, from a similar viewpoint, $R^{14}$ and $R^{15}$ are each preferably a methyl group and an ethyl group.

No particular limitation is imposed on $Z^-$ as long as it is an anionic group. Specific examples thereof include an alkyl sulfate ion, a sulfate ion, a phosphate ion, alkyl carboxylate ion, and a halide ion. Among them, from the viewpoint of easiness of production and availability, a halide ion is preferable. Examples of the halide ion include a fluoride ion, a chloride ion, a bromide ion, and an iodide ion, and from the viewpoint of chemical stability, a chloride ion and a bromide ion are preferable, of which a chloride ion is more preferable.

From the viewpoint of improving rinse feel, from the viewpoint of improving combing property of the hair during rinsing when the cleansing composition of the present invention is applied to the hair, and imparting softness to the hair, and from the viewpoint of imparting a refreshing feeling to the skin when the cleansing composition of the present invention is applied to the body, the content of the component (C) in the cleansing composition of the present invention is preferably 50% by mass or less in the cleansing composition of the present invention, more preferably 30% by mass or less, more preferably 20% by mass or less, more preferably 15% by mass or less, more preferably 10% by mass or less, and even more preferably 5% by mass or less. From the viewpoint of improving an appearance and stability of the cleansing composition, and of improving lathering, foam quality and durability of foam, the content of the component (C) is preferably 0.5% by mass or more, more preferably 1% by mass or more, and even more preferably 2% by mass or more.

From the viewpoint of improving a durability of foam and rinse feel when a treatment is performed with the cleansing composition of the present invention, as well as from the viewpoint of improving combing property of the hair during rinsing when the cleansing composition of the present invention is applied to the hair, and imparting the softness to the hair, and from the viewpoint of imparting a refreshing feeling to the skin when the cleansing composition is applied to the body, the mass content ratio of the component (A) to the component (C) [component (A)/component (C)] is preferably from 1000 to 0.1, more preferably from 100 to 1, more preferably from 50 to 2, and even more preferably from 20 to 3.

<Other Components>

The cleansing composition of the present invention may contain, in addition to the aforementioned components, water, which may serve as a medium in the production of the component (A), a viscosity reducing agent, polyhydric alcohols, a preservative, and a reducing agent, and also, other components used as ordinary cosmetic raw materials. Examples of the component include a feel improver, a thickener, a fragrance, an ultraviolet absorber, a visible light absorbent, a chelating agent, an antioxidant, a coloring agent, a preservative, a pH adjuster, a viscosity regulator, a pearlescent agent, and a moisturizing agent.

<Production Method of the Cleansing Composition for Skin or Hair>

No particular limitation is imposed on the production method of the cleansing composition of the present invention, and it may be produced by a conventional method. Specifically, for example, in the case of a liquid shampoo for hair, water, the aforementioned component (A), the aforementioned component (B), and if necessary, the aforementioned component (C) are heated and mixed to homogeneity. If necessary, the aforementioned component (A) may be dispersed or dissolved in water in advance, and then added. The cleansing composition of the present invention may also be prepared by adding the aforementioned component (A) to an aqueous solution of a surfactant and homogeneously dissolving or dispersing it, followed by cooling, and if necessary, adding a pearlescent agent, a pH adjuster, a fragrance, a dye, and the like.

No particular limitation is also imposed on the form of the cleansing composition of the present invention, and it can be provided in any form such as a liquid, a foam, a paste, a cream, a solid, and a powder, among which a liquid, a paste, or a cream is preferable, and a liquid is more preferable. When the cleansing composition is provided as a liquid, polyethylene glycol, ethanol, and the like are preferably used as a liquid medium in addition to water. The content of water in the cleansing composition of the present invention is preferably 10% by mass or more and 95% by mass or less.

<Intended Use and Method of Use>

The cleansing composition of the present invention can impart not only an excellent durability of foam and rinse feel and good combing property and softness to hair during rinsing, but also a refreshing feeling to skin; therefore, it can be preferably used as a cleansing composition for hair or a cleansing composition for skin. Specific examples of the cleansing composition for hair include a hair shampoo. Specific examples of the cleansing composition for skin include a body shampoo, a facial cleanser, a makeup remover, or a hand soap.

Because the cleansing composition of the present invention can impart not only an excellent durability of foam and rinse feel and good combing property and softness to hair during rinsing, but also a refreshing feeling to skin, a method for washing the hair which includes applying the aforementioned cleansing agent for skin or hair of the present invention to hair, followed by washing and then rinsing is also provided. Also, a method for washing the body which includes applying the aforementioned cleansing agent of the present invention to a surface of the skin, followed by washing and rinsing is also provided. It should be that a method for applying the cleansing agent of the present invention to the skin or the hair, a washing method, and a rinsing method are not particularly limited, and various methods may be applied.

Pertaining to the aforementioned embodiments, the present invention further discloses the following cleansing agent for skin or hair and a method for washing the hair and a method for washing the body using the above cleansing agent for skin or hair.

[1] A cleansing composition for skin or hair, comprising the following (A) and (B):

(A) an internal olefin sulfonate composition containing an internal olefin sulfonate having 12 or more and 24 or less carbon atoms; and (B) an anionic surfactant having no sulfate group except the internal olefin sulfonate (A) and an anionic surfactant having two or more carboxylic acid groups.

[2] The cleansing composition for skin or hair according to the aforementioned [1], wherein the number of carbon atoms in the internal olefin sulfonate is preferably 14 or more, more preferably 16 or more, and is preferably 20 or less, and more preferably 18 or less.

[3] The cleansing composition for skin or hair according to the aforementioned [1] or [2], wherein the mass content ratio (internal olefin sulfonate having 16 carbon atoms/internal olefin sulfonate having 18 carbon atoms) of an internal olefin sulfonate having 16 carbon atoms to an internal olefin sulfonate having 18 carbon atoms in the component (A) is preferably from 50/50 to 99/1, more preferably from 60/40 to 95/5, more preferably from 70/30 to 90/10, more preferably from 75/25 to 90/10, more preferably from 75/25 to 85/15, and even more preferably from 78/22 to 85/15.

[4] The cleansing composition for skin or hair according to any one of the aforementioned [1] to [3], wherein the total content of an internal olefin sulfonate having 16 carbon atoms and an internal olefin sulfonate having 18 carbon atoms in the component (A) is preferably 50% by mass or more, more preferably 60% by mass, more preferably 70% by mass, more preferably 80% by mass or more, more preferably 90% by mass or more, and even more preferably 95% by mass or more.

[5] The cleansing composition for skin or hair according to any one of the aforementioned [1] to [4], wherein the content of an internal olefin sulfonate in which a sulfonate group is present at the C-2 position in the component (A) is preferably 25% by mass or less, more preferably 24% by mass or less, more preferably 23% by mass or less, more preferably 22% by mass or less, more preferably 20% by mass or less, more preferably less than 20% by mass, more preferably 19% by mass or less, and even more preferably 18% by mass or less.

[6] The cleansing composition for skin or hair according to any one of the aforementioned [1] to [5], wherein a content of an internal olefin sulfonate in which a sulfonate group is present at a C-2 position in the component (A) is preferably 5% by mass or more and 25% by mass or less, more preferably 5% by mass or more and 24% by mass or less, more preferably 5% by mass or more and 23% by mass or less, more preferably 5% by mass or more and 22% by mass or less, preferably 5% by mass or more and 20% by mass or less, more preferably 6% by mass or more and less than 20% by mass, more preferably 7% by mass or more and 19% by mass or less, more preferably 8% by mass or more and 18% by mass or less, and even more preferably 9% by mass or more and 17.5% by mass or less.

[7] The cleansing composition for skin or hair according to any one of the aforementioned [1] to [6], wherein a content of the internal olefin sulfonate in which a sulfonate group is present at the C-2 position in the component (A) is preferably 9% by mass or more and 17.5% by mass or less, more preferably 9% by mass or more and 15% by mass or less, more preferably 9% by mass or more and 12% by mass or less, and even more preferably 9% by mass or more and 10% by mass or less.

[8] The cleansing composition for skin or hair according to any one of the aforementioned [1] to [7], wherein a content of the internal olefin sulfonate in which a sulfonate group is present at the C-2 position in the component (A) is preferably 9% by mass or more and 18% by mass or less, more preferably 10% by mass or more and 18% by mass or less, more preferably 12% by mass or more and 18% by mass or less, more preferably 14% by mass or more and 18% by mass or less, and even more preferably 16% by mass or more and 18% by mass or less.

[9] The cleansing composition for skin or hair according to any one of the aforementioned [1] to [8], wherein the content of an internal olefin sulfonate in which a sulfonate group is present at the C-2 position in the component (A) is preferably 5% by mass or more, more preferably 6% by mass or more, more preferably 7% by mass or more, more preferably 8% by mass or more, more preferably 9% by mass or more, more preferably 10% by mass or more, more preferably 12% by mass or more, more preferably 14% by mass or more, and even more preferably 16% by mass or more.

[10] The cleansing composition for skin or hair according to any one of the aforementioned [1] to [9], wherein the content of an internal olefin sulfonate in which the sulfonate group is present at the C-2 position in the component (A) is preferably 20% by mass or less, more preferably less than 20% by mass, more preferably 19% by mass or less, more preferably less than 18% by mass, even more preferably 17.5% by mass or less, and is preferably 5% by mass or more, more preferably 6% by mass or more, more preferably 7% by mass or more, more preferably 8% by mass or more, and even more preferably 9% by mass or more.

[11] The cleansing composition for skin or hair according to any one of the aforementioned [1] to [10], wherein the content of an internal olefin sulfonate in which the sulfonate group is present at the C-1 position of the olefin chain or alkane chain in the component (A) is preferably 3.0% by mass or less, more preferably 2.5% by mass or less, more preferably 2.0% by mass or less, more preferably 1.5% by mass or less, even more preferably 1.0% by mass or less, and is preferably 0.01% by mass or more.

[12] The cleansing agent for skin or hair according to any one of the aforementioned [1] to [11], wherein the mass content ratio (hydroxy form/olefin form) of the hydroxy form of an internal olefin sulfonate to the olefin form of an internal olefin sulfonate in the component (A) is preferably from 50/50 to 100/0, more preferably from 60/40 to 100/0, more preferably from 70/30 to 100/0, more preferably from 75/25 to 100/0, and even more preferably from 75/25 to 95/5.

[13] The cleansing composition for skin or hair according to any one of the aforementioned [1] to [12], wherein when the component (A) is obtained by a sulfonation of a raw material internal olefin, followed by neutralization and then hydrolysis, the content of an internal olefin in which the double bond is present at the C-2 position in the raw material internal olefin is preferably 40% by mass or less, more preferably 35% by mass or less, more preferably 32% by mass or less, and even more preferably 30% by mass or less, and preferably 5% by mass or more, more preferably 6% by mass or more, more preferably 7% by mass or more, more preferably 8% by mass or more, more preferably 9% by mass or more, more preferably 12% by mass or more, and even more preferably 15% by mass or more.

[14] The cleansing composition for skin or hair according to any one of the aforementioned [1] to [13], wherein when the component (A) is obtained by a sulfonation of the raw material internal olefin, followed by neutralization and then hydrolysis, a content of the internal olefin in which the double bond is present at a C-2 position in the raw material internal olefin is preferably 5% by mass or more and 40% by mass or less, more preferably 5% by mass or more and 35% by mass or less, more preferably 5% by mass or more and 32% by mass or less, more preferably 5% by mass or more and 30% by mass or less, preferably 6% by mass or more and 30% by mass or less, more preferably 7% by mass or more and 30% by mass or less, more preferably 8% by mass or more and 30% by mass or less, more preferably 9% by mass or more and 30% by mass or less, more preferably 12% by mass or more and 30% by mass or less, and even more preferably 15% by mass or more and 27% by mass or less.

[15] The cleansing composition for skin or hair according to any one of the aforementioned [1] to [14], wherein when the component (A) is obtained by a sulfonation of the raw material internal olefin, followed by neutralization and then hydrolysis, a content of the internal olefin in which the double bond is present at a C-2 position in the raw material internal olefin is preferably 15% by mass or more and 25% by mass or less, more preferably 15% by mass or more and 20% by mass or less, more preferably 15% by mass or more and less than 20% by mass, more preferably 15% by mass or more and 19% by mass or less, and even more preferably 15% by mass or more and 18% by mass or less.

[16] The cleansing composition for skin or hair according to any one of the aforementioned [1] to [15], wherein when the component (A) is obtained by a sulfonation of the raw material internal olefin, followed by neutralization and then hydrolysis, a content of the internal olefin in which the double bond is present at a C-2 position in the raw material internal olefin is preferably 20% by mass or more and 27% by mass or less, more preferably 22% by mass or more and 27% by mass or less, and even more preferably 24% by mass or more and 27% by mass or less.

[17] The cleansing composition for skin or hair according to any one of the aforementioned [1] to [16], wherein the content of the component (A) in the cleansing composition is preferably 0.1% by mass or more, more preferably 1% by mass or more, more preferably 2% by mass or more, even more preferably 5% by mass or more, and is preferably 80% by mass or less, more preferably 50% by mass or less, more preferably 30% by mass or less, and even more preferably 20% by mass or less.

[18] The cleansing composition for skin or hair according to any, one of the aforementioned [1] to [17], wherein a content of the raw material internal olefin in the component (A) is preferably less than 5.0% by mass, more preferably less than 3.0% by mass, more preferably less than 1.5% by mass, and even more preferably less than 1.0% by mass in the component (A).

[19] The cleansing composition for skin or hair according to any one of the aforementioned [1] to [18], wherein a content of the inorganic compounds in the component (A) is preferably less than 7.5% by mass, more preferably less than 5.0% by mass, more preferably less than 3.0% by mass, more preferably less than 2.0% by mass, and even more preferably less than 1.6% by mass in the component (A).

[20] The cleansing composition for skin or hair according to any one of the aforementioned [1] to [19], wherein the component (B) is preferably the anionic surfactant having one carboxylic acid group or the anionic surfactant having a sulfonic acid group, more preferably one or more selected from the fatty acid, the alkyl ether acetic acid of Formula (I), the alkylsarcosine, the alkylglycine, the alkylalanine, the sulfosuccinic acid, the α-olefinsulfonic acid, the secondary alkane sulfonate, the linear alkylbenzene sulfonic acid, the alkylisethionate, the alkyl sulfo acetic acid, and the salts thereof, and even more preferably one or more selected from the secondary alkane sulfonate, the alkylisethionate, the alkyl sulfo acetic acid, the fatty acid, the alkyl ether acetic acid of Formula (I), the alkylsarcosine, the sulfosuccinic acid, and the salts thereof.

[21] The cleansing composition for skin or hair according to any one of the aforementioned [1] to [20], wherein the component (B) is preferably an anionic surfactant represented by any of following Formulas (I) to (VI):

$$R^1—O—(CH_2CH_2O)n^1—CH_2—COOM \quad (I)$$

(wherein $R^1$ represents an alkyl group having 4 or more and 22 or less carbon atoms; $n^1$ represents a number of 4.0 or more and 16 or less; and M represents a hydrogen atom, an alkali metal, an alkaline earth metal (½ atom), ammonium, or organic ammonium);

(II)

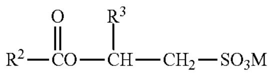

(wherein $R^2$ represents an alkyl group having 4 or more and 22 or less carbon atoms; $R^3$ represents a hydrogen atom or an alkyl group having from 1 to 4 carbon atoms; and M represents a hydrogen atom, an alkali metal, an alkaline earth metal (½ atom), ammonium, or organic ammonium);

(III)

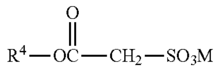

(wherein $R^4$ represents an alkyl group having 4 or more and 22 or less carbon atoms, and M represents a hydrogen atom, an alkali metal, an alkaline earth metal (½ atom), ammonium, or organic ammonium);

(IV)

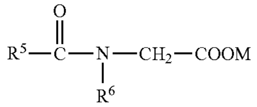

(wherein $R^5$ represents an alkyl group having 8 or more and 22 or less carbon atoms; $R^6$ represents a hydrogen atom or an alkyl group having from 1 to 4 carbon atoms; and M represents a hydrogen atom, an alkali metal, an alkaline earth metal (½ atom), ammonium, or organic ammonium);

(V)

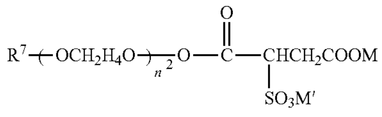

(wherein $R^7$ represents an alkyl group having 8 or more and 22 or less carbon atoms; $n^2$ represents a number of 0 or more and 3 or less; and M and M' each independently represent a hydrogen atom, an alkali metal, an alkaline earth metal (½ atom), ammonium, or organic ammonium); and $$R^8—COOM \quad (VI)$$

(wherein $R^8$ represents an alkyl group having 8 or more and 22 or less carbon atoms; and M represents a hydrogen atom, an alkali metal, an alkaline earth metal (½ atom), ammonium, or organic ammonium).

[22] The cleansing composition for skin or hair according to any one of the aforementioned [1] to [21], wherein the content of the component (B) is preferably 0.01% by mass or more, more preferably 0.05% by mass or more, more preferably 0.5% by mass or more, more preferably 2% by mass or more, and even more preferably 4% by mass or more, and the content is preferably 30% by mass or less, more preferably 20% by mass or less, more preferably 15% by mass or less, more preferably 10% by mass or less, and even more preferably 8% by mass or less.

[23] The cleansing composition for skin or hair according to any one of the aforementioned [1] to [22], wherein the mass content ratio of the component (A) to the component (B) [component (A)/component (B)] is preferably from 0.01 to 100, more preferably from 0.05 to 20, more preferably from 0.1 to 10, more preferably from 0.2 to 6, more preferably from 0.3 to 6, and even more preferably from 0.5 to 6.

[24] The cleansing composition for skin or hair according to any one of the aforementioned [1] to [23], further comprising the surfactant (C) other than the component (A) and the component (B).

[25] The cleansing composition for skin or hair according to the aforementioned [24], wherein the component (C) is preferably the anionic surfactant, the non-ionic surfactant, or the ampholytic surfactant other than the component (A) and the component (B).

[26] The cleansing composition for skin or hair according to the aforementioned [25], wherein the anionic surfactant other than the component (A) and the component (B) is preferably one or two or more selected from the ester sulfate, the sulfonate, the carboxylate, the ester phosphate, and the amino acid salt.

[27] The cleansing composition for skin or hair according to any one of the aforementioned [24] to [26], wherein the content of the anionic surfactant containing the sulfate group in the component (C) is preferably 10% by mass or less, more preferably 3.0% by mass or less, and even more preferably 0.5% by mass or less; and the cleansing composition contains no anionic surfactant containing the sulfate group except for a case where the anionic surfactant is inevitably mixed.

[28] The cleansing composition for skin or hair according to any one of the aforementioned [24] to [27], wherein the content of the component (C) is preferably 50% by mass or less, more preferably 30% by mass or less, more preferably 20% by mass or less, more preferably 15% by mass or less, more preferably 10% by mass or less, and even more preferably 5% by mass or less; and the content is preferably 0.5% by mass or more, more preferably 1% by mass or more, and even more preferably 2% by mass or more.

[29] The cleansing composition for skin or hair according to any one of the aforementioned [24] to [28], wherein the mass content ratio of the component (A) to the component (C) [component (A)/component (C)] is preferably from 1000 to 0.1, more preferably from 100 to 1, more preferably from 50 to 2, and even more preferably from 20 to 3.

[30] A method for washing the hair, comprising applying the cleansing composition for skin or hair according to any one of the aforementioned [1] to [29] to hair, followed by washing and then rinsing.

[31] A method for washing the body, comprising applying the cleansing composition for skin or hair according to any one of the aforementioned [1] to [29] to a surface of the skin, followed by washing and then rinsing.

[32] A method for imparting to hair combing property and softness during rinsing, comprising applying the cleansing composition for skin or hair according to any one of the aforementioned [1] to [29] to hair.

[33] A method for imparting refreshing feeling to skin, comprising applying the cleansing composition for skin or hair according to any one of the aforementioned [1] to [29] to skin.

[34] The cleansing composition for skin or hair according to any one of the aforementioned [1] to [29] for washing hair.

[35] The cleansing composition for skin or hair according to any one of the aforementioned [1] to [29] for washing skin.

[36] Use of the cleansing composition for skin or hair according to any one of the aforementioned [1] to [29] for washing hair.

[37] Use of the cleansing composition for skin or hair according to any one of the aforementioned [1] to [29] for washing skin.

[38] The cleansing composition for skin or hair according to any one of the aforementioned [1] to [29] for imparting to hair combing property and softness during rinsing.

[39] The cleansing composition for skin or hair according to any one of the aforementioned [1] to [29] for imparting refreshing feeling to skin.

[40] Use of the cleansing composition for skin or hair according to any one of the aforementioned [1] to [29] for imparting to hair combing property and softness during rinsing.

[41] Use of the cleansing composition for skin or hair according to any one of the aforementioned [1] to [29] for imparting refreshing feeling to skin.

[42] The cleansing composition for skin or hair according to any one of the aforementioned [1] to [29] for improving foam durability.

[43] The cleansing composition for skin or hair according to any one of the aforementioned [1] to [29] for improving rinse feel.

EXAMPLES

Hereinbelow, the present invention will be specifically described with reference to Examples. It should be noted that unless otherwise specifically noted, "part" means "part by mass" and "%" means "% by mass" in the following Examples and Comparative Examples. Also, the methods used for measuring various physical properties are as follows.

(1) Conditions of Measurement (i) Method for Measuring the Position of a Double Bond in the Raw Material Internal Olefin The position of a double bond in a raw material internal olefin was measured by gas chromatography (hereinbelow, abbreviated as GC). Specifically, an internal olefin was converted to a dithiated derivative by reaction with dimethyl disulfide, and each component was separated by GC. As a result, the position of a double bond in an internal olefin was found based on the peak area of each component.

The apparatus and analytical conditions used for the measurement are as follows. GC apparatus (trade name: HP6890, the product of Hewlett-Packard Company); Column (trade name: Ultra-Alloy-1HT capillary column, 30 m×250 μm×0.15 μm, the product of Frontier Laboratories Ltd.); Detector (flame ionization detector (FID)); Injection temperature of 300° C.; Detector temperature of 350° C.; and He flow rate of 4.6 mL/minute.

(ii) Method for Measuring the Mass Ratio of Hydroxy Form/Olefin Form

The mass ratio of hydroxy form/olefin form of the internal olefin sulfonate was measured by HPLC-MS. Specifically, the hydroxy form and the olefin form were separated by HPLC and each form was identified by separately analyzing with MS. As a result, from the resulting HPLC-MS peak area, the fraction of each form was obtained.

The apparatus and analytical conditions used for the measurement are as follows. HPLC apparatus (trade name: Agilent technology 1100, the product of Agilent Technologies, Inc.); Column (trade name: L-column ODS 4.6×150 mm, the product of Chemicals Evaluation and Research Institute, Japan); Sample preparation (diluted 1000-fold with methanol); Eluent A (10 mM ammonium acetate in water); Eluent B (10 mM ammonium acetate in methanol), Gradient (0 minute (A/B=30/70%)→10 minutes (30/70%)→55 minutes (0/100%)→65 minutes (0/100%)→66 minutes (30/70%)→75 minutes (30/70%)); MS apparatus (trade name: Agilent technology 1100 MS SL (G1946D)); and MS detection (anion detection m/z 60-1600, UV 240 nm).

(iii) Method for Measuring the Content of the Raw Material Internal Olefin

The content of the raw material internal olefin of the internal olefin sulfonate was measured by GC. Specifically, ethanol and petroleum ether were added to an aqueous solution of internal olefin sulfonate, followed by extraction to give olefin in the petroleum ether phase. As a result, from the GC peak area of the olefin, the amount thereof was quantitated. The apparatus and analytical conditions used for the measurement are as follows. GC apparatus (trade name: Agilent technology 6850, the product of Agilent Technologies, Inc.); Column (trade name: Ultra-Alloy-1HT capillary column, 15 m×250 μm×0.15 μm, the product of Frontier Laboratories, Ltd.); Detector (flame ionization detector (FID)); Injection temperature of 300° C.; Detector temperature of 350° C.; and He flow rate of 3.8 mL/minute.

(iv) Method for Measuring the Content of Inorganic Compounds

The content of inorganic compounds was measured by potentiometric titration and neutralization titration. Specifically, the content of $Na_2SO_4$ was quantitated by measuring sulfate ion ($SO_4^{2-}$) by potentiometric titration. Also, the content of NaOH was quantitated by neutralization titration with diluted hydrochloric acid.

(v) Method for Measuring the Content of the Paraffin Component

The content of the paraffin component was measured by GC. Specifically, ethanol and petroleum ether were added to an aqueous solution of internal olefin sulfonate, followed by extraction to give paraffin in the petroleum ether phase. As a result, from the GC peak area of the paraffin, the amount thereof was quantitated. It should be noted that the apparatus and analytical conditions used for measurement are the same as those used for the measurement of the content of the raw material internal olefin.

(vi) Method for Measuring the Content of Internal Olefin Sulfonate in which a Sulfonate Group is Present at a C-2 Position The linkage position of the sulfonate group was measured by GC. Specifically, the resulting internal olefin sulfonate (A) was reacted with trimethylsilyldiazomethane to form a methyl-esterified derivative. Then, each component was separated by GC. Each of a peak area was regarded as a mass ratio, and the content of internal olefin sulfonate in which a sulfonate group is present at a C-2 position was quantitated.

The apparatus and analytical conditions used for the measurement are as follows. GC apparatus (trade name: Agilent technology 6850, the product of Agilent Technologies, Inc.); Column (trade name: HP-1 capillary column, 30 m×320 μm×0.25 μm, the product of Agilent Technologies, Inc.); Detector (hydrogen flame ionization detector (FID)); Injection temperature of 300° C.; Detector temperature of 300° C.; He flow rate of 1.0 mL/min.; Oven (60° C. (0 min.)→10° C./min.→300° C. (10 min.)).

(2) Production of an Internal Olefin

Production Example A

Into a flask with a stirrer, 7000 g (25.9 moles) of 1-octadecanol (trade name: KALCOL 8098, the product of Kao Corporation), and as a solid acid catalyst, 1050 g (15 wt % relative to the raw material alcohol) of γ-alumina (STREM Chemicals, Inc.) were placed, and reactions were allowed to proceed for 13 hours at 285° C. while stirring and passing nitrogen (7000 mL/minute) through the system. The alcohol conversion ratio was 100% and the purity of C18 internal olefin was 98.5% after the completion of the reaction. The resulting crude internal olefin was transferred to a distillation flask and distilled at from 148 to 158° C./0.5 mmHg, whereby 100% pure internal olefin having 18 carbon atoms was obtained. The double bond distribution in the resulting internal olefin was 0.7% by mass at C-1 position, 16.9% by mass at C-2 position, 15.9% by mass at C-3 position, 16.0% by mass at C-4 position, 14.7% by mass at C-5 position, 11.2% by mass at C-6 position, 10.2% by mass at C-7 position, and 14.6% by mass in total at C-8 and 9 positions.

Production Example B

Into a flask with a stirrer, 7000 g (28.9 moles) of 1-hexadecanol (trade name: KALCOL 6098, the product of Kao Corporation), and as a solid acid catalyst, 700 g (10% by mass relative to the raw material alcohol) of γ-alumina (STREM Chemicals, Inc.) were placed, and reactions were allowed to proceed for five hours at 280° C. while stirring and passing nitrogen (7000 mL/minute) through the system. The alcohol conversion ratio was 100%, and the purity of C16 internal olefin was 99.7% after the completion of the reaction. The resulting crude internal olefin was transferred to a distillation flask and distilled at from 136 to 160° C./4.0 mmHg, whereby 100% pure internal olefin having 16 carbon atoms was obtained. The double bond distribution in the resulting internal olefin was 0.5% by mass at C-1 position, 16.5% by mass at C-2 position, 15.4% by mass at C-3 position, 16.4% by mass at C-4 position, 17.2% by mass at C-5 position, 14.2% by mass at C-6 position, and 19.8% by mass in total at C-7 and 8 positions.

Production Example C

Into a flask with a stirrer, 7000 g (28.9 moles) of 1-hexadecanol (trade name: KALCOL 6098, the product of Kao Corporation), and as a solid acid catalyst, 700 g (10 wt % relative to the raw material alcohol) of γ-alumina (STREM Chemicals, Inc.) were placed, and reactions were allowed to proceed for three hours at 280° C. while stirring and passing nitrogen (7000 mL/minute) through the system. The alcohol conversion ratio was 100%, and the purity of C16 internal olefin was 99.6% after the completion of the reaction. The resulting crude internal olefin was transferred to a distillation flask and distilled at from 136 to 160° C./4.0 mmHg, whereby 100% pure internal olefin having 16 carbon atoms was obtained. The double bond distribution in the resulting internal olefin was 1.8% by mass at C-1 position, 30.4% by mass at C-2 position, 23.9% by mass at C-3 position, 16.8% by mass at C-4 position, 12.0% by mass at C-5 position, 7.4% by mass at C-6 position, and 7.8% by mass in total at C-7 and 8 positions.

Production Example D

Into a flask with a stirrer, 7000 g (25.9 moles) of 1-octadecanol (trade name: KALCOL 8098, the product of Kao Corporation), and as a solid acid catalyst, 700 g (10 wt % relative to the raw material alcohol) of γ-alumina (STREM Chemicals, Inc.) were placed, and reactions were allowed to proceed for 10 hours at 280° C. while stirring and passing nitrogen (7000 mL/minute) through the system. The alcohol conversion ratio was 100%, and the purity of C18 internal olefin was 98.2% after the completion of the reaction. The resulting crude internal olefin was transferred to a distillation flask and distilled at the temperature inside of from 148 to 158° C./0.5 mmHg, whereby 100% pure internal olefin having 18 carbon atoms was obtained. The double bond distribution in the resulting internal olefin was 0.8% by mass at C-1 position, 31.3% by mass at C-2 position, 22.9% by mass at C-3 position, 15.5% by mass at C-4 position, 10.8% by mass at C-5 position, 7.2% by mass at C-6 position, 5.3% by mass at C-7 position, and 6.2% by mass in total at C-8 and C-9 positions.

Production Example E

A reaction time was adjusted in a same manner as Production Example C, in order to produce C16 internal olefin having 100% of purity. The double bond distribution of the resulting internal olefin was 0.8% by mass at a C-1 position, 26.8% by mass at a C-2 position, 22.6% by mass at a C-3 position, 18.2% by mass at a C-4 position, 16.5% by mass at a C-5 position, 8.5% by mass at a C-6 position, and 6.6% by mass in total at C-7 and C-8 positions.

Production Example F

A reaction time was adjusted in a same manner as Production Example D, in order to produce C18 internal olefin having 100% of purity. The double bond distribution of the resulting internal olefin was 0.3% by mass at a C-1 position, 19.0% by mass at a C-2 position, 17.6% by mass at a C-3 position, 17.4% by mass at a C-4 position, 14.9% by mass at a C-5 position, 12.3% by mass at a C-6 position, 8.8% by mass at a C-7 position, and 9.8% by mass in total at C-8 and C-9 positions.

Production Example G 11.9 kg of the C16 internal olefin obtained in the Production Example E and 3.1 kg of the C18 internal olefin obtained in Production Example F were mixed to produce 15.0 kg of C16/C18 (mass ratio of 79.4/20.6) internal olefin. The double bond distribution of the resulting internal olefin was 0.7% by mass at a C-1 position, 25.2% by mass at a C-2 position, 21.6% by mass at a C-3 position, 18.0% by mass at a C-4 position, 16.2% by mass at a C-5 position, 9.3% by mass at a C-6 position, 4.4% by mass at a C-7 position, 3.6% by mass at a C-8 position, and 1.0% by mass at a C-9 position.

Production Example H

A reaction time was adjusted in a same manner as Production Example C, in order to produce C16 internal olefin having 100% of purity. The double bond distribution of the resulting internal olefin was 0.5% by mass at a C-1 position, 30.1% by mass at a C-2 position, 25.5% by mass at a C-3 position, 18.9% by mass at a C-4 position, 11.1% by mass at a C-5 position, 7.0% by mass at a C-6 position, and 7.0% by mass in total at C-7 and C-8 positions.

Production Example I

A reaction time was adjusted in a same manner as Production Example D, in order to produce C18 internal olefin having 100% of purity. The double bond distribution of the resulting internal olefin was 0.5% by mass at a C-1 position, 25.0% by mass at a C-2 position, 22.8% by mass at a C-3 position, 19.1% by mass at a C-4 position, 14.0% by mass at a C-5 position, 7.4% by mass at a C-6 position, 5.4% by mass at a C-7 position, and 5.8% by mass in total at C-8 and C-9 positions.

Production Example J

Into a flask with a stirrer, 6000 g (30.6 moles) of 1-tetradecene (trade name: LINEALENE 14, the product of Idemitsu Kosan Co., Ltd.), and as a solid acid catalyst, 173 g (2.9 wt % relative to the raw material 1-tetradecene) of β-zeolite (Zeolyst International, Inc.) were placed, and reactions were allowed to proceed for 21 hours at 120° C. while stirring and passing nitrogen (200 mL/minute) through the system. The internal isomerization ratio of α-olefin was 99.0%, and the purity of C14 internal olefin was 91.1% after the completion of the reaction. The resulting crude internal olefin was transferred to a distillation flask and distilled at from 130 to 136° C./from 12.8 to 13.5 mmHg, whereby 100% pure internal olefin having 14 carbon atoms was obtained. The double bond distribution of the resulting internal olefin was 1.3% by mass at C-1 position, 31.8% by mass at C-2 position, 23.8% by mass at C-3 position, 21.0% by mass at C-4 position, 8.6% by mass at C-5 position, and 13.6% by mass in total at C-6 and C-7 positions.

Production Example K

Into a flask with a stirrer, 6000 g (35.6 moles) of 1-dodecene (trade name: LINEALENE 12, the product of Idemitsu Kosan Co., Ltd.), and as a solid acid catalyst, 180 g (3.0 wt % relative to the raw material 1-dodecene) of β-zeolite (Zeolyst International, Inc.) were placed, and reactions were allowed to proceed for 12.5 hours at 120° C. while stirring and passing nitrogen (200 mL/minute) through the system. The internal isomerization ratio of α-olefin was 98.4%, and the purity of C12 internal olefin was 92.1% after the completion of the reaction. The resulting crude internal olefin was transferred to a distillation flask and distilled at from 134 to 138° C./from 75.0 to 78.8 mmHg, whereby 100% pure internal olefin having 12 carbon atoms was obtained. The double bond distribution of the resulting internal olefin was 0.5% by mass at C-1 position, 33.1% by mass at C-2 position, 23.7% by mass at C-3 position, 21.2% by mass at C-4 position, 15.0% by mass at C-5 position, and 6.8% by mass at C-6 position.

(3) Production of an Internal Olefin Sulfonate

Production Example 1

Using a thin film sulfonation reactor (14 mm in inner diameter and 4 m in length), the sulfonation reaction of the internal olefin having 16 carbon atoms produced in Production Example C was carried out by passing through sulfur trioxide gas containing a concentration of $SO_3$ at 2.8% by volume, while passing cooling water of 20° C. through the outer jacket of the reactor. It should be noted that the reaction molar ratio of $SO_3$/internal olefin was set at 1.09.

The resulting sulfonate was added to an alkaline aqueous solution containing 1.2 times the molar amount of sodium hydroxide relative to the theoretical acid value (AV), followed by neutralization at 30° C. for one hour while stirring. The resulting neutralized product was hydrolyzed by heating at 160° C. for one hour in an autoclave, whereby a crude product of sodium C16 internal olefin sulfonate was obtained.

Then, 300 g of the crude product thus obtained was transferred to a separatory funnel, to which 300 mL of ethanol was added. Then, 300 mL of petroleum ether was added per operation, whereby oil-soluble impurities were removed by extraction. At this time, inorganic compounds (mainly composed of sodium sulfate) which were precipitated at the oil-water interface by the addition of ethanol were also separated and removed from the aqueous phase by the oil-water separation operation. The above operation was repeated three times. Then, the aqueous phase side was evaporated to dryness, whereby sodium internal olefin sulfonate (1) having 16 carbon atoms was obtained. The content of the raw material internal olefin was less than 100 ppm (below the GC detection limit) and that of inorganic compounds was 1.9% by mass. The above results are shown in Table 1.

Production Example 2

Except for using the internal olefin having 18 carbon atoms produced in Production Example D, sodium internal olefin sulfonate (2) having 18 carbon atoms was obtained under the same conditions as those used in Production Example 1. The content of the raw material internal olefin was less than 100 ppm (below the GC detection limit) and that of inorganic compounds was 0.9% by mass. The above results are shown in Table 1.

Production Example 3

Except for using the internal olefin having 16 carbon atoms produced in Production Example B, sodium internal olefin sulfonate (3) having 16 carbon atoms was obtained under the same conditions as those used in Production Example 1. The content of the raw material internal olefin was less than 100 ppm (below the GC detection limit) and that of inorganic compounds was 1.3% by mass. The above results are shown in Table 1.

Production Example 4

Except for using the internal olefin having 18 carbon atoms produced in Production Example A, sodium internal olefin sulfonate (4) having 18 carbon atoms was obtained under the same conditions as those used in Production Example 1. The content of the raw material internal olefin was less than 100 ppm (below the GC detection limit) and that of inorganic compounds was 1.7% by mass. The above results are shown in Table 1.

Production Example 5

The C16/18 internal olefin (the content of internal olefin in which double bonds are present at C-2 position is 25.2% by mass) obtained in Production Example G was used as a raw material, and a sodium C16/C18 internal olefin sulfonate (5) was obtained by the same manner as in Production Example 1. The mass ratio of hydroxy form (sodium hydroxyalkane sulfonate)/olefin form (sodium olefin sulfonate) in the obtained sodium internal olefin sulfonate was 87/13. Also, the content of the raw material internal olefin contained in the obtained sodium internal olefin sulfonate was less than 100 ppm (below the GC detection limit) and that of inorganic compounds was 0.5% by mass.

Production Example 6

Except for using the internal olefin having 16 carbon atoms produced in Production Example H, sodium internal olefin sulfonate (6) having 16 carbon atoms was obtained under the same conditions as those used in Production Example 1. The content of the raw material internal olefin was less than 100 ppm (below the GC detection limit) and that of inorganic compounds was 0.2% by mass. The above results are shown in Table 1.

Production Example 7

Except for using the internal olefin having 18 carbon atoms produced in Production Example I, sodium internal olefin sulfonate (7) having 18 carbon atoms was obtained under the same conditions as those used in Production Example 1. The content of the raw material internal olefin was less than 100 ppm (below the GC detection limit) and that of inorganic compounds was 0.1% by mass. The above results are shown in Table 1.

Production Example 8

Except for using the internal olefin having 14 carbon atoms produced in Production Example J, sodium internal olefin sulfonate (8) having 14 carbon atoms was obtained under the same conditions as those used in Production Example 1. The content of the raw material internal olefin was less than 100 ppm (below the GC detection limit) and that of inorganic compounds was 0.5% by mass. The above results are shown in Table 1.

Production Example 9

Except for using the internal olefin having 12 carbon atoms produced in Production Example K, sodium internal olefin sulfonate (9) having 12 carbon atoms was obtained under the same conditions as those used in Production Example 1. The content of the raw material internal olefin was less than 100 ppm (below the GC detection limit) and that of inorganic compounds was 0.2% by mass. The above results are shown in Table 1.

TABLE 1

| | Raw material internal olefin | | Internal olefin sulfonate | |
|---|---|---|---|---|
| | Number of carbon atoms | C-2 Double bond (%) | HAS/IOS (Mass ratio) | Content of internal olefin sulfonate in which sulfonate group is present at C-2 position (%) |
| Internal olefin sulfonate (1) | C16 | 30.4 | 80/20 | 20.3 |
| Internal olefin sulfonate (2) | C18 | 31.3 | 80/20 | 21.4 |
| Internal olefin sulfonate (3) | C16 | 16.5 | 80/20 | 9.3 |
| Internal olefin sulfonate (4) | C18 | 16.9 | 80/20 | 9.6 |
| Internal olefin sulfonate (5) | C16/C18 | 25.2 | 87/13 | 17.6 |
| Internal olefin sulfonate (6) | C16 | 30.1 | 80/20 | 19.9 |

TABLE 1-continued

| | Raw material internal olefin | | Internal olefin sulfonate | |
|---|---|---|---|---|
| | Number of carbon atoms | C-2 Double bond (%) | HAS/IOS (Mass ratio) | Content of internal olefin sulfonate in which sulfonate group is present at C-2 position (%) |
| Internal olefin sulfonate (7) | C18 | 25.0 | 80/20 | 15.0 |
| Internal olefin sulfonate (8) | C14 | 31.8 | 92.8/7.4 | 22.0 |
| Internal olefin sulfonate (9) | C12 | 33.1 | 80/20 | 21.0 |

(4) Preparation of the Cleansing Compositions

Using internal olefin sulfonates shown in Table 1, the cleansing compositions for hair or skin each having the compositions shown in from Tables 2 to 4 were prepared by a conventional method. Specifically, the component (A), the component (B), and appropriate amounts of water, and if necessary, the component (C) were placed in a beaker. The resulting mixture was heated to 60° C. and mixed, and then cooled to room temperature. Then, the mixture was supplemented with water and adjusted to pH 6 with a pH adjuster (a 50% aqueous solution of citric acid or a 10% aqueous solution of sodium hydroxide), whereby each cleansing composition was obtained.

(5) Hair Evaluation after Washing

Each of the following components was placed in a beaker and heated to 80° C., followed by mixing. After confirming homogeneous dissolution, the mixture was cooled to give a plain shampoo. Octadecyloxy propyl trimethylammonium chloride and stearyl alcohol in the following composition were placed into a beaker (A), and were heated to 80° C. to melt them. On the other hand, purified water and methylparaben were placed into the other beaker (B), and were heated to 80° C. while stirring. They were confirmed to be uniformly dissolved. Then, the mixed solution in the beaker (A) was added into the beaker (B) while stirring the purified water and methylparaben in the beaker (B) at 80° C., and emulsification was then performed for 30 minutes. Heating was stopped, and the beaker (B) was cooled to room temperature to obtain a plain rinse.

After a hair bundle (Japanese hair which is not subjected to processings such as bleach and hair coloring, about 20 cm, 15 g) was washed with the obtained plain shampoo, the obtained plain rinse was applied to the hair bundle. After the plain rinse was applied and worked into the hair bundle during 1 minute, the hair bundle was rinsed to obtain an evaluation tress.

(Composition of the Plain Shampoo)

| (Component) | (% by mass) |
|---|---|
| Sodium polyoxyethylene lauryl ether sulfate (42.0% as EMAL E-27C (the product of Kao Corporation, active content, 27% by mass)) | 11.3 |
| Coconut oil fatty acid N-methyl ethanolamide (AMINON C-11S (the product of Kao Corporation)) | 3.0 |
| Citric acid | 0.2 |
| Methylparaben | 0.3 |
| Purified water | Balance |
| Total | 100.0 |

(Composition of the Plain Rinse)

| (Component) | (% by mass) |
|---|---|
| Octadecyloxy propyl trimethylammonium chloride (6.7% as QUARTAMIN E-80K (the product of Kao Corporation, active content, 45% by mass)) | 3.0 |
| Stearyl alcohol (KALCOL 8098 (the product of Kao Corporation)) | 6.0 |
| Methylparaben | 0.3 |
| Purified water | Balance |
| Total | 100.0 |

The tress for evaluation thus obtained was washed with each cleansing composition, and was evaluated for the rinse speed after washing, combing property of the hair during rinsing, and softness by five expert panelists based on the following evaluation criteria and evaluation method.

Also, in order to evaluate a foam retention (durability) in the presence of an oily component such as stain of sebum, 0.05 ml of model sebum was applied to the hair, and was washed. Then, foam durability during washing was evaluated. The model sebum was prepared by uniformly mixing 4/1% by mass of triolein/lanolin at 40° C.

The results are shown in Tables 2 and 3.

(Evaluation Criteria and Evaluation Method)

Rinse Speed

5: Very fast rinse
4: Fast rinse
3: Normal speed rinse (equivalent to Comparative Example 1)
2: Slow rinse
1: Very slow rinse Combing Property 5: Very good combing
4: Good combing
3: Normal combing (equivalent to Comparative Example 7)
2: Poor combing
1: Very poor combing Softness of Hair 5: Very soft
4: Soft
3: Fair (equivalent to Comparative Example 7)
2: Hard
1: Very hard Foam Durability 5: Foam durability is very good (not feeling a decrease in the volume of foam during washing)
4: Foam durability is good (less decrease in the volume of foam)
3: Normal foam durability (equivalent to Comparative Example 7)
2: Foam durability was poor (remarkable decrease in the volume of foam)
1: Foam was not maintained (defoaming was found during washing)

TABLE 2

| Cleansing composition for hair (shampoo) | | | Examples 1 | 2 | 3 | 4 | 5 | 6 | 7 | 8 | 9 | 10 | 11 |
|---|---|---|---|---|---|---|---|---|---|---|---|---|---|
| Formulation (part by mass) | (A) | Internal olefin sulfonate(1) | 6.0 | | | | | | | | | | |
| | | Internal olefin sulfonate(2) | | 6.0 | | | | | | | | | |
| | | Internal olefin sulfonate(3) | | | 6.0 | | 5.5 | 4.8 | 4.0 | 3.0 | 8.0 | 0.8 | 16 |
| | | Internal olefin sulfonate(4) | | | | 6.0 | 0.5 | 1.2 | 2.0 | 3.0 | 2.0 | 0.2 | 4.0 |
| | | Internal olefin sulfonate(5) | | | | | | | | | | | |
| | | Internal olefin sulfonate(6) | | | | | | | | | | | |
| | | Internal olefin sulfonate(7) | | | | | | | | | | | |
| | | Internal olefin sulfonate(8) | | | | | | | | | | | |
| | | Internal olefin sulfonate(9) | | | | | | | | | | | |
| | | Sodium lauryl sulfate *1 | | | | | | | | | | | |
| | (B) | Sodium α-olefin sulfonate *2 | | | | | | | | | | | |
| | | Secondary alkane sulfonate *3 | | | | | | | | | | | |
| | | Sodium lauryl ether acetate *4 | 6.0 | 6.0 | 6.0 | 6.0 | 6.0 | 6.0 | 6.0 | 6.0 | 2.0 | 11 | 2.0 |
| | | Sodium lauryl ether sulfonate *5 | | | | | | | | | | | |
| | | pH Adjuster | | | | | | q.s. | | | | | |
| | | Purified water | | | | | | Balance | | | | | |
| | Content of internal olefin in which double bond is present at C-2 position in raw material internal olefin (% by mass) | | 30.4 | 31.3 | 16.5 | 16.9 | 16.5 | 16.6 | 16.6 | 16.7 | 16.6 | 16.6 | 16.6 |
| | Content of C16/C18 in component (A) (% by mass) | | 100 | 100 | 100 | 100 | 100 | 100 | 100 | 100 | 100 | 100 | 100 |
| | Content of internal olefin sulfonate in which sulfonate group is present at C-2 position (% by mass) | | 20.3 | 21.4 | 9.3 | 9.6 | 9.3 | 9.4 | 9.4 | 9.5 | 9.4 | 9.4 | 9.4 |
| Evaluation results | | Rinse speed | 4.2 | 3.6 | 4.8 | 4.2 | 5.0 | 5.0 | 5.0 | 4.8 | 5.0 | 4.4 | 5.0 |
| | | Combing property of hair during rinsing | 4.0 | 4.0 | 4.2 | 4.6 | 4.4 | 4.6 | 4.4 | 4.2 | 4.2 | 4.6 | 4.4 |
| | | Softness of hair during rinsing | 3.8 | 4.6 | 4.2 | 5.0 | 4.4 | 4.8 | 4.8 | 4.8 | 4.6 | 4.2 | 4.6 |
| | | Durability of foam | — | — | — | — | — | 3.2 | — | — | — | — | — |

| Cleansing composition for hair (shampoo) | | | Examples 12 | 13 | 14 | 15 | 16 | 17 | 18 | 19 | 20 | 21 | 22 |
|---|---|---|---|---|---|---|---|---|---|---|---|---|---|
| Formulation (part by mass) | (A) | Internal olefin sulfonate(1) | | | | | | | | | | | |
| | | Internal olefin sulfonate(2) | | | | | | | | | | | |
| | | Internal olefin sulfonate(3) | 2.0 | | | | | | | | | | |
| | | Internal olefin sulfonate(4) | 0.5 | | | | | | | | | | |
| | | Internal olefin sulfonate(5) | | 6.0 | | | | | | | | | |
| | | Internal olefin sulfonate(6) | | | 6.0 | | 5.5 | 4.8 | 4.0 | 3.0 | 8.0 | 2.4 | 1.4 |
| | | Internal olefin sulfonate(7) | | | | 6.0 | 0.5 | 1.2 | 2.0 | 3.0 | 2.0 | 0.6 | 0.4 |
| | | Internal olefin sulfonate(8) | | | | | | | | | | 3.0 | 4.2 |
| | | Internal olefin sulfonate(9) | | | | | | | | | | | |
| | | Sodium lauryl sulfate *1 | | | | | | | | | | | |
| | (B) | Sodium α-olefin sulfonate *2 | | | | | | | | | | | |
| | | Secondary alkane sulfonate *3 | | | | | | | | | | | |
| | | Sodium lauryl ether acetate *4 | 1.0 | 6.0 | 6.0 | 6.0 | 6.0 | 6.0 | 6.0 | 6.0 | 2.0 | 6.0 | 6.0 |
| | | Sodium lauryl ether sulfonate *5 | | | | | | | | | | | |
| | | pH Adjuster | | | | | | q.s. | | | | | |
| | | Purified water | | | | | | Balance | | | | | |
| | Content of internal olefin in which double bond is present at C-2 position in raw material internal olefin (% by mass) | | 16.6 | 25.2 | 30.1 | 25.0 | 29.7 | 29.1 | 28.4 | 27.6 | 29.1 | 30.4 | 31.0 |
| | Content of C16/C18 in component (A) (% by mass) | | 100 | 100 | 100 | 100 | 100 | 100 | 100 | 100 | 100 | 50 | 30 |
| | Content of internal olefin sulfonate in which sulfonate group is present at C-2 position (% by mass) | | 9.4 | 17.6 | 19.9 | 15 | 19.5 | 18.9 | 18.3 | 17.5 | 18.9 | 20.5 | 21.1 |
| Evaluation results | | Rinse speed | 4.8 | 4.8 | 4.4 | 4.0 | 4.6 | 4.8 | 4.6 | 4.4 | 4.8 | 4.8 | 5.0 |
| | | Combing property of hair during rinsing | 4.4 | 4.2 | 4.0 | 4.6 | 4.2 | 4.2 | 4.2 | 4.2 | 4.2 | 4.2 | 4.2 |
| | | Softness of hair during rinsing | 3.6 | 5.0 | 4.2 | 4.6 | 4.6 | 4.8 | 4.8 | 4.6 | 4.8 | 4.0 | 3.8 |
| | | Durability of foam | — | 4.6 | 4.2 | 3.8 | 4.4 | 4.6 | 4.4 | 4.2 | 4.8 | 4.2 | 4.2 |

| Cleansing composition for hair (shampoo) | | | Examples 23 | 24 | Comparative Examples 1 | 2 | 3 | 4 | 5 | 6 | 7 |
|---|---|---|---|---|---|---|---|---|---|---|---|
| Formulation (part by mass) | (A) | Internal olefin sulfonate(1) | | | | | | | | | |
| | | Internal olefin sulfonate(2) | | | | 12.0 | | | | | |
| | | Internal olefin sulfonate(3) | | | | | | | | | |
| | | Internal olefin sulfonate(4) | | | | | | | | | |
| | | Internal olefin sulfonate(5) | | | | | | | | | |
| | | Internal olefin sulfonate(6) | | | | | | | | | |

TABLE 2-continued

| | | | | | | | | | | | |
|---|---|---|---|---|---|---|---|---|---|---|---|
| | | Internal olefin sulfonate(7) | | | | | | | | | |
| | | Internal olefin sulfonate(8) | 6.0 | | | | | | | | |
| | | Internal olefin sulfonate(9) | | 6.0 | | | | | | | |
| | | Sodium lauryl sulfate *1 | | | | | 12.0 | | | | |
| | (B) | Sodium α-olefin sulfonate *2 | | | | | | 6.0 | | 6.0 | |
| | | Secondary alkane sulfonate *3 | | | | | | | 6.0 | 6.0 | |
| | | Sodium lauryl ether acetate *4 | 6.0 | 6.0 | 12.0 | | | 6.0 | 6.0 | | 6.0 |
| | | Sodium lauryl ether sulfonate *5 | | | | | | | | | 6.0 |
| | | pH Adjuster | | | | q.s. | | | | | |
| | | Purified water | | | | Balance | | | | | |
| | Content of internal olefin in which double bond is present at C-2 position in raw material internal olefin (% by mass) | | 31.8 | 33.1 | | | | | | | |
| | Content of C16/C18 in component (A) (% by mass) | | 0 | 0 | | | | | | | |
| | Content of internal olefin sulfonate in which sulfonate group is present at C-2 position (% by mass) | | 22 | 21 | | | | | | | |
| Evaluation results | | Rinse speed | 5.0 | 5.0 | 3.0 | 3.2 | 2.0 | 4.0 | 2.4 | 3.2 | 3.0 |
| | | Combing property of hair during rinsing | 4.2 | 4.2 | 4.0 | 2.6 | 1.8 | 2.0 | 3.6 | 2.4 | 3.0 |
| | | Softness of hair during rinsing | 3.8 | 3.8 | 3.0 | 3.6 | 1.2 | 1.8 | 4.0 | 3.4 | 3.0 |
| | | Durability of foam | 4.2 | 4.0 | — | — | — | — | — | — | 3.0 |

*1 The product of Kao Corporation, trade name: EMAL 0
*2 The product of Lion Corporation, trade name: LIPOLAN PB-800 (active ingredient 95%)
*3 The product of LANXESS K.K., trade name: Mersolat H95 (active ingredient 95%)
*4 The product of Kao Corporation, trade name: KAO AKYPO RLM-45NV (active ingredient 23.5%)
*5 The product of Kao Corporation, trade name: 17.14% of EMAL 270S (effective component of 70%) was added

TABLE 3

| | | | Examples | | | | | | | | | | | | | |
|---|---|---|---|---|---|---|---|---|---|---|---|---|---|---|---|---|
| Cleansing composition for hair (shampoo) | | | 25 | 26 | 27 | 28 | 29 | 30 | 31 | 32 | 33 | 34 | 35 | 36 | 37 | 38 |
| Formulation (part by mass) | (A) | Internal olefin sulfonate(3) | 4.8 | 4.8 | 4.8 | 4.8 | 4.8 | 4.8 | 4.8 | | | | | | | |
| | | Internal olefin sulfonate(4) | 1.2 | 1.2 | 1.2 | 1.2 | 1.2 | 1.2 | 1.2 | | | | | | | |
| | | Internal olefin sulfonate(6) | | | | | | | | 4.8 | 4.8 | 4.8 | 4.8 | 4.8 | 4.8 | 4.8 |
| | | Internal olefin sulfonate(7) | | | | | | | | 1.2 | 1.2 | 1.2 | 1.2 | 1.2 | 1.2 | 1.2 |
| | (B) | Sodium lauryl ether acetate *1 | 6.0 | | | | | | | 6.0 | | | | | | |
| | | Sodium cocoyl isethionate *2 | | 6.0 | | | | | | | 6.0 | | | | | |
| | | Sodium lauryl sulfoacetate *3 | | | 6.0 | | | | | | | 6.0 | | | | |
| | | Sodium sulfosuccinate *4 | | | | 6.0 | | | | | | | 6.0 | | | |
| | | Lauroyl sarcosine *5 | | | | | 6.0 | | | | | | | 6.0 | | |
| | | Sodium α-olefin sulfonate *6 | | | | | | 6.0 | | | | | | | 6.0 | |
| | | Secondary alkane sulfonate *7 | | | | | | | 6.0 | | | | | | | 6.0 |
| | | pH Adjuster | | | | | | | q.s. | | | | | | | |
| | | Purified water | | | | | | | Balance | | | | | | | |
| Evaluation results | | Rinse speed | 4.6 | 5.0 | 4.4 | 4.6 | 5.0 | 4.8 | 3.8 | 4.6 | 5.0 | 4.4 | 4.6 | 5.0 | 4.6 | 3.8 |
| | | Combing property of hair during rinsing | 4.4 | 4.4 | 4.4 | 4.6 | 4.0 | 3.6 | 4.4 | 4.4 | 4.2 | 4.2 | 4.2 | 4.0 | 3.6 | 4.6 |
| | | Softness of hair during rinsing | 5.0 | 4.2 | 4.4 | 5.0 | 4.6 | 3.6 | 4.4 | 5.0 | 4.2 | 4.4 | 4.8 | 4.6 | 3.8 | 4.6 |
| | | Durability of foam | — | — | — | — | — | — | — | 4.0 | 5.0 | 4.8 | 4.2 | 5.0 | 5.0 | 4.4 |

*1 The product of Kao Corporation, trade name: KAO AKYPO RLM-100NV (active ingredient: 23.5%)
*2 The product of NOF CORPORATION, trade name: Diapon CI
*3 The product of Nikko Chemicals, Co., Ltd., trade name: LSA-F (active ingredient: 96%)
*4 The product of TOHO Chemical Industry Co., Ltd., trade name: Kohacool L-300 (active ingredient: 30%)
*5 The product of Kawaken Fine Chemicals Co. Ltd., trade name: Soypon SLE (active ingredient: 30%)
*6 The product of Lion Corporation, trade name: UPOLAN LB-440 (active ingredient: 36%)
*7 The product of LANXESS, trade name: Mersolat H95 (active ingredient: 95%)

(6) Skin Evaluation after Washing

Five expert panelists washed their hands with each cleansing composition, and evaluated the rinse speed after washing, and the refreshing feeling to the skin after towel drying, and durability of foam based on the following evaluation criteria and evaluation method. It should be noted that the rinse speed was evaluated based on the same criteria as those used for hair. Also, durability of foam was evaluated based on the same criteria as those used for hair by applying model sebum to the hand. The results are shown in Table 4.

Refreshing Feeling

5: Very refreshing

4: Refreshing

3: Fair (equivalent to Comparative Example 7)

2: Not refreshing

1: Not refreshing at all and feels stickiness

TABLE 4

| Cleansing composition for skin (body shampoo) | | | Examples 39 | 40 | 41 | 42 | 43 | 44 | 45 | 46 | 47 | 48 | 49 |
|---|---|---|---|---|---|---|---|---|---|---|---|---|---|
| Formulation (part by mass) | (A) | Internal olefin sulfonate(3) | | 4.8 | 4.0 | 3.0 | 8.0 | 0.8 | 16.0 | 2.0 | 4.8 | 4.8 | 4.8 |
| | | Internal olefin sulfonate(4) | 6.0 | 1.2 | 2.0 | 3.0 | 2.0 | 0.2 | 4.0 | 0.5 | 1.2 | 1.2 | 1.2 |
| | | Internal olefin sulfonate(5) | | | | | | | | | | | |
| | | Internal olefin sulfonate(6) | | | | | | | | | | | |
| | | Internal olefin sulfonate(7) | | | | | | | | | | | |
| | | Sodium lauryl sulfate *1 | | | | | | | | | | | |
| | (B) | Sodium α-olefin sulfonate *2 | | | | | | | | | | | |
| | | Secondary alkane sulfonate *3 | | | | | | | | | | | 6.0 |
| | | Sodium lauryl ether acetate *4 | 6.0 | 6.0 | 6.0 | 6.0 | 2.0 | 11.0 | 2.0 | 1.0 | | 3.0 | |
| | | C12-16 fatty acid sodium salt *5 | | | | | | | | | 5.0 | | |
| | | Coconut oil fatty acid monoethanolamide *6 | | | | | | | | | 1.0 | | |
| | | Decyl glucoside *7 | | | | | | | | | | 3.0 | |
| | | Sodium lauryl ether sulfonate *8 | | | | | | | | | | | |
| | | pH Adjuster | | | | | | q.s. | | | | | |
| | | Purified water | | | | | | Balance | | | | | |
| | Content of internal olefin in which double bond is present at C-2 position in raw material internal olefin (% by mass) | | 16.9 | 16.6 | 16.6 | 16.7 | 16.6 | 16.6 | 16.6 | 16.6 | 16.6 | 16.6 | 16.6 |
| | Content of C16/C18 in component (A) (% by mass) | | 100 | 100 | 100 | 100 | 100 | 100 | 100 | 100 | 100 | 100 | 100 |
| | Content of internal olefin sulfonate in which sulfonate group is present at C-2 position (% by mass) | | 9.6 | 9.4 | 9.4 | 9.5 | 9.4 | 9.4 | 9.4 | 9.4 | 9.4 | 9.4 | 9.4 |
| Evaluation results | | Rinse speed | 4.0 | 5.0 | 4.6 | 4.4 | 4.6 | 4.0 | 5.0 | 4.2 | 4.8 | 4.6 | 3.8 |
| | | Refreshing feeling after towel drying | 4.2 | 4.6 | 4.6 | 4.4 | 4.2 | 3.8 | 4.4 | 4.0 | 4.4 | 4.6 | 4.0 |
| | | Durability of foam | — | 3.2 | — | — | — | — | — | — | — | — | — |

| Cleansing composition for skin (body shampoo) | | | Examples 50 | 51 | 52 | 53 | 54 | 55 | 56 | 57 | 58 | 59 | 60 |
|---|---|---|---|---|---|---|---|---|---|---|---|---|---|
| Formulation (part by mass) | (A) | Internal olefin sulfonate(3) | | | | | | | | | | | |
| | | Internal olefin sulfonate(4) | | | | | | | | | | | |
| | | Internal olefin sulfonate(5) | 6.0 | | | | | | | | | | |
| | | Internal olefin sulfonate(6) | | 6.0 | | 4.8 | 4.0 | 3.0 | 8.0 | 0.8 | 16.0 | 2.0 | 4.8 |
| | | Internal olefin sulfonate(7) | | | 6.0 | 1.2 | 2.0 | 3.0 | 2.0 | 0.2 | 4.0 | 0.5 | 1.2 |
| | | Sodium lauryl sulfate *1 | | | | | | | | | | | |
| | (B) | Sodium α-olefin sulfonate *2 | | | | | | | | | | | |
| | | Secondary alkane sulfonate *3 | | | | | | | | | | | |
| | | Sodium lauryl ether acetate *4 | 6.0 | 6.0 | 6.0 | 6.0 | 6.0 | 6.0 | 2.0 | 11.0 | 2.0 | 1.0 | |
| | | C12-16 fatty acid sodium salt *5 | | | | | | | | | | | 5.0 |
| | | Coconut oil fatty acid monoethanolamide *6 | | | | | | | | | | | 1.0 |
| | | Decyl glucoside *7 | | | | | | | | | | | |
| | | Sodium lauryl ether sulfonate *8 | | | | | | | | | | | |
| | | pH Adjuster | | | | | | q.s. | | | | | |
| | | Purified water | | | | | | Balance | | | | | |
| | Content of internal olefin in whichdouble bond is present at C-2 position in raw material internal olefin (% by mass) | | 25.2 | 30.1 | 25.0 | 29.1 | 28.4 | 27.6 | 29.1 | 29.1 | 29.1 | 29.1 | 29.1 |
| | Content of C16/C18 in component (A) (% by mass) | | 100 | 100 | 100 | 100 | 100 | 100 | 100 | 100 | 100 | 100 | 100 |
| | Content of internal olefin sulfonate in which sulfonate group is present at C-2 position (% by mass) | | 17.6 | 19.9 | 15 | 18.9 | 18.3 | 17.5 | 18.9 | 18.9 | 18.9 | 18.9 | 18.9 |
| Evaluation results | | Rinse speed | 4.8 | 4.8 | 4.0 | 4.6 | 4.4 | 4.2 | 4.6 | 3.8 | 4.8 | 4.2 | 4.6 |
| | | Refreshing feeling after towel drying | 5.0 | 4.8 | 4.2 | 4.8 | 4.8 | 4.6 | 4.2 | 3.8 | 4.6 | 4.0 | 4.6 |
| | | Durability of foam | 4.4 | 4.4 | 3.6 | 4.4 | 4.2 | 4.0 | 4.6 | 3.6 | 5.0 | 2.4 | 4.6 |

TABLE 4-continued

| Cleansing composition for skin (body shampoo) | | | Examples 61 | 62 | Comparative Examples 1 | 3 | 4 | 5 | 8 | 7 |
|---|---|---|---|---|---|---|---|---|---|---|
| Formulation (part by mass) | (A) | Internal olefin sulfonate(3) | | | | | | | | |
| | | Internal olefin sulfonate (4) | | | | | | | | |
| | | Internal olefin sulfonate(5) | | | | | | | | |
| | | Internal olefin sulfonate (6) | 4.8 | 4.8 | | | | | | |
| | | Internal olefin sulfonate(7) | 1.2 | 1.2 | | | | | | |
| | | Sodium lauryl sulfate *1 | | | | 12.0 | | | | |
| | (B) | Sodium α-olefin sulfonate *2 | | | | | 6.0 | | | |
| | | Secondary alkane sulfonate *3 | | 6.0 | | | | 6.0 | 6.0 | |
| | | Sodium lauryl ether acetate *4 | 3.0 | | 12.0 | | 6.0 | 6.0 | 3.0 | 6.0 |
| | | C12-16 fatty acid sodium salt *5 | | | | | | | | |
| | | Coconut oil fatty acid monoethanolamide *6 | | | | | | | | |
| | | Decyl glucoside *7 | 3.0 | | | | | | 3.0 | |
| | | Sodium lauryl ether sulfonate *8 | | | | | | | | 6.0 |
| | | pH Adjuster | | | | q.s. | | | | |
| | | Purified water | | | | Balance | | | | |
| | Content of internal olefin in which double bond is present at C-2 position in raw material internal olefin (% by mass) | | 29.1 | 29.1 | | | | | | |
| | Content of C16/C18 in component (A) (% by mass) | | 100 | 100 | | | | | | |
| | Content of internal olefin sulfonate in which sulfonate group is present at C-2 position (% by mass) | | 18.9 | 18.9 | | | | | | |
| Evaluation results | | Rinse speed | 4.4 | 3.6 | 3.0 | 1.8 | 4.2 | 2.0 | 3.4 | 3.6 |
| | | Refreshing feeling after towel drying | 4.6 | 4.0 | 3.0 | 5.0 | 3.0 | 2.0 | 2.6 | 3.0 |
| | | Durability of foam | 4.0 | 4.4 | — | — | — | — | — | 3.0 |

*1 The product of Kao Corporation, trade name: EMAL 0
*2 The product of Lion Corporation, trade name: UPOLAN LB-440 (active ingredient, 36%)
*3 The product of LANXESS, trade name: Mersolat H95 (active ingredient, 95%)
*4 The product of Kao Corporation: trade name, KAO AKYPO RLM-45NV (active ingredient, 23.5%)
*5 The product of Kao Corporation: trade name, PRIOLY B-100 (active ingredient, 35%)
*6 The product of Kawaken Fine Chemicals Co. Ltd.: trade name, Amisol CME
*7 The product of Kao Corporation: trade name, MYDOL 10 (active ingredient, 40%)
*8 The product of Kao Corporation, trade name: 17.14% of EMAL 270S (effective component of 70%) was added

Example 63 and Comparative Example 8 (Hair Shampoo)

A hair shampoo having the composition shown in Table 5 was produced in a similar manner to Example 1, and was evaluated in a similar manner to Example 1. The results are shown in Table 5.

TABLE 5

| Cleansing composition for hair (hair shampoo) | | Examples 63 | Comp. Ex. 8 |
|---|---|---|---|
| (A) | Internal olefin sulfonate (6) | 2.0 | 2.0 |
| | Internal olefin sulfonate (7) | 0.5 | 0.5 |
| (B) | Sodium lauryl ether acetate * 1 | 3.0 | |
| | N-Acyl-N-glutamic acid TEA *2 | | 3.0 |
| | Lauric acid amidopropyl betaine *3 | 3.0 | 3.0 |
| | POE(20)lauryl ether *4 | 1.0 | 1.0 |
| | POE(15)isostearyl ether *5 | 1.0 | 1.0 |
| | pH Adjuster | q.s. | |
| | Purified water | Balance | |
| Evaluation results | Rinse speed | 4.2 | 3.0 |
| | Combing property of hair during rinsing | 3.6 | 3.0 |
| | Softness of hair during rinsing | 4.0 | 3.0 |
| | Durability of foam | 3.2 | 3.0 |

* 1 The product of Kao Corporation, trade name: KAO AKYPO RLM-100NV (active ingredient: 23.5%)
*2 The product of Ajinomoto Co., Inc, trade name: AMISOFT CT12S(active ingredient: 30%)
*3 The product of Kao Corporation, trade name: AMPHITOL 20AB (active ingredient: 30%)
*4 The product of Kao Corporation, trade name: EMULGEN 123
*5 The product of Kao Corporation, trade name: EMULGEN 320P

Example 64 and Comparative Example 9 (Hair Shampoo)

A hair shampoo having the composition shown in Table 6 was produced in a similar manner to Example 1, and was evaluated in a similar manner to Example 1. The results are shown in Table 6.

TABLE 6

| Cleansing composition for hair (hair shampoo) | | Examples 64 | Comp. Ex. 9 |
|---|---|---|---|
| (A) | Internal olefin sulfonate (6) | 8.0 | 8.0 |
| (B) | Sodium lauryl ether acetate * 1 | 8.0 | |
| | POE(3)lauryl ether *2 | | 8.0 |
| | Lauric acid diethanolamide *3 | 2.0 | 2.0 |
| | Lauryl dimethyl betaine *4 | 2.0 | 2.0 |
| | pH Adjuster | q.s. | |
| | Purified water | Balance | |
| Evaluation results | Rinse speed | 4.8 | 3.0 |
| | Combing property of hair during rinsing | 4.0 | 3.0 |
| | Softness of hair during rinsing | 3.2 | 3.0 |
| | Durability of foam | 4.2 | 3.0 |

* 1 The product of Kao Corporation, trade name: KAO AKYPO RLM-100NV (active ingredient: 23.5%)
*2 The product of Kao Corporation, trade name: EMULGEN 103
*3 The product of Kao Corporation, trade name: AMINON L-02
*4 The product of Kao Corporation, trade name: AMPHITOL 24B Example 65 (Hair Shampoo)

A hair shampoo having the following composition was produced in a similar manner to Example 1, and was evaluated in a similar manner to Example 1.

| (Components) | (% by mass) |
|---|---|
| Sodium internal olefin sulfonate (3) | 8.0 |
| Sodium internal olefin sulfonate (4) | 2.0 |
| Coconut oil fatty acid amidopropyl betaine | 1.4 |
| Coconut oil fatty acid monoethanolamide | 0.6 |
| Sodium polyoxyethylene (4.5) lauryl ether acetate *1 | 3.8 |
| Ethylene glycol distearate *2 | 1.0 |
| Fragrance, sodium benzoate | q.s. |
| Purified water | Balance |
| Total | 100.0 |

*1: Add 16.2% of KAO AKYPO RLM-45NV (active component: 23.5%) manufactured by Kao Corporation
*2: Add 5% of PEARL CONCENTRATE FC-1 (active component: 20%) manufactured by Kao Corporation This hair shampoo had an excellent rinse feel, and had a feeling upon application having excellent combing property during rinsing and excellent softness of hair.

Example 66 (Hair Shampoo)

A hair shampoo having the following composition was produced in a similar manner to Example 1, and was evaluated in a similar manner to Example 1.

| (Components) | (% by mass) |
|---|---|
| Sodium internal olefin sulfonate (3) | 6.0 |
| Sodium internal olefin sulfonate (4) | 1.5 |
| Lauryldimethyl betaine aminoacetate *1 | 1.1 |
| Coconut oil fatty acid monoisopropanol amide | 1.5 |
| Sodium lauryl methyl isethionate *2 | 6.0 |
| Fragrance, methylparaben | q.s. |
| Purified water | Balance |
| Total | 100.0 |

*1: Add 3.8% of AMPHITOL 20BS (active component: 30%) manufactured by Kao Corporation
*2: Add 20% of Iselux LQ-CLR (active component: 30%) manufactured by Innospec Inc.

This hair shampoo had an excellent rinse feel, and had a feeling upon application having good combing property during rinsing and good softness of hair.

Example 67 (Hair Shampoo)

A hair shampoo having the following composition was produced in a similar manner to Example 1, and was evaluated in a similar manner to Example 1.

| (Components) | (% by mass) |
|---|---|
| Sodium internal olefin sulfonate (3) | 6.0 |
| Sodium internal olefin sulfonate (4) | 1.5 |
| Sodium α-olefin sulfonate *1 | 5.0 |
| Coconut oil fatty acid amidopropyl betaine | 3.0 |
| Coconut oil fatty acid methylethanolamide *2 | 2.0 |
| Lauric acid *3 | 0.5 |
| Fragrance, sodium benzoate | q.s. |
| Purified water | Balance |
| Total | 100.0 |

*1: Add 13.9% of LIPOLAN LB-440 (active component: 36%) manufactured by Lion Corporation
*2: AMINON C-11S manufactured by Kao Corporation
*3: LUNAC L-98 manufactured by Kao Corporation This hair shampoo had an excellent rinse feel, and had a feeling upon application having good combing property during rinsing and good softness of hair.

Example 68 (Hair Shampoo)

A hair shampoo having the following composition was produced in a similar manner to Example 1, and was evaluated in a similar manner to Example 1.

| (Components) | (% by mass) |
|---|---|
| Sodium internal olefin sulfonate (3) | 10.0 |
| Sodium internal olefin sulfonate (4) | 2.5 |
| Coconut oil fatty acid amidopropyl betaine *1 | 0.75 |
| Coconut oil fatty acid diethanolamide | 2.0 |
| Octadecyloxy propyl trimethylammonium chloride *2 | 0.3 |
| Sodium sulfosuccinate *3 | 3.0 |
| Fragrance, sodium benzoate, lactic acid (pH adjuster) | q.s. |
| Purified water | Balance |
| Total | 100.0 |

*1: Add 2.5% of AMPHITOL 55AB (active component: 30%) manufactured by Kao Corporation
*2: Add 0.67% of QUARTAMIN E-80K (active component: 45%) manufactured by Kao Corporation
*3: Add 10.0% of Kohacool L-400 (active component: 30%) manufactured by TOHO Chemical Industry Co., Ltd.

This hair shampoo had an excellent rinse feel, and had a feeling upon application having good combing property during rinsing and good softness of hair.

Example 69 (Facial Cleanser)

A facial cleanser having the following composition was produced in a similar manner to Example 1, and was evaluated in a similar manner to the evaluation of the cleansing composition for skin of Example 39.

| (Components) | (% by mass) |
|---|---|
| Sodium internal olefin sulfonate (3) | 10.0 |
| Sodium internal olefin sulfonate (4) | 2.5 |
| Coconut oil fatty acid monoethanolamide | 2.0 |
| Coconut oil fatty acid *1 | 3.0 |
| Cocamidopropyl betaine | 5.0 |
| pH adjuster | q.s. |
| Purified water | Balance |
| Total | 100.0 |

*1: trade name; LUNAC L-55 manufactured by Kao Corporation

This facial cleanser had an excellent rinse feel, and had a feeling upon application having an excellent refreshing feeling after towel drying.

Example 70 (Body Shampoo)

A body shampoo having the following composition was produced in a similar manner to Example 1, and was evaluated in a similar manner to the evaluation of the cleansing composition for skin of Example 39.

| (Components) | (% by mass) |
|---|---|
| Sodium internal olefin sulfonate (3) | 10.0 |
| Sodium internal olefin sulfonate (4) | 2.5 |
| Lauric acid *1 | 6.5 |
| Coconut oil fatty acid amidopropyl betaine | 2.0 |
| Glycerol | 3.0 |
| Fragrance, methylparaben | q.s. |
| Purified water | Balance |
| Total | 100 |

*1: Add 17.14% of PRIOLY B-100 (active component: 35%) manufactured by Kao Corporation This body shampoo had an excellent rinse feel, and had a feeling upon application having an excellent refreshing feeling after towel drying.

Example 71 (Hand Soap)

A hand soap having the following composition was produced in a similar manner to Example 1, and was evaluated in a similar manner to the evaluation of the cleansing composition for skin of Example 39.

| (Components) | (% by mass) |
|---|---|
| Sodium internal olefin sulfonate (3) | 8.0 |
| Sodium internal olefin sulfonate (4) | 2.0 |
| Coconut oil fatty acid amidopropyl betaine *1 | 3.0 |
| Glycerol | 3.0 |
| Sodium polyoxyethylene (4.5) lauryl ether acetate *2 | 6.0 |
| Fragrance, methylparaben | q.s. |
| Purified water | Balance |
| Total | 100.0 |

*1: Add 10.0% of AMPHITOL 55AB (active component: 30%) manufactured by Kao Corporation.
*2: Add 25.6% of KAO AKYPO RLM-45NV (active component: 23.5%) manufactured by Kao Corporation This hand soap had an excellent rinse feel, and had a feeling upon application having an excellent refreshing feeling after towel drying.

INDUSTRIAL APPLICABILITY

The cleansing composition for skin or hair of the present invention can be favorably used in the fields of hair shampoo, body shampoo, facial cleanser, makeup remover, and hand soap, and the like, and further, it is also favorably applicable to animals such as dogs and cats sensitive to stimulus.

The invention claimed is:

1. A method for washing hair, comprising:
applying a cleansing composition to hair; and
washing and then rinsing the hair, wherein
the cleansing composition comprises:
(A) an internal olefin sulfonate having 12 or more and 24 or less carbon atoms; and
(B) an anionic surfactant, excluding a surfactant having a sulfate group or having two or more carboxylic acid groups,
wherein a total content of an internal olefin sulfonate having 16 carbon atoms and an internal olefin sulfonate having 18 carbon atoms in the internal olefin sulfonate (A) is 95% by mass or more based on the total mass of the internal olefin sulfonate (A), wherein a content of an internal olefin sulfonate in which a sulfonate group is present at a C-2 position in the internal olefin sulfonate (A) is 5% to 25% by mass based on the total mass of the internal olefin sulfonate (A), and
wherein a mass content ratio of an internal olefin sulfonate having 16 carbon atoms to an internal olefin sulfonate having 18 carbon atoms in the internal olefin sulfonate (A) is from 78/22 to 90/10 (an internal olefin sulfonate having 16 carbon atoms/an internal olefin sulfonate having 18 carbon atoms).

2. The method for washing hair according to claim 1, wherein the cleansing composition is applied to the hair to impart thereto a hair combing property and softness during rinsing.

3. The method for washing hair according to claim 1,
wherein the component (B) is an anionic surfactant represented by any of following Formulae (I) to (VI):

$$R^1—O—(CH_2CH_2O)n^1—CH_2—COOM \qquad (I)$$

wherein $R^1$ represents an alkyl group having 4 or more and 22 or less carbon atoms; $n^1$ represents a number of 4.0 or more and 16 or less; and M represents a hydrogen atom, an alkali metal, an alkaline earth metal, ammonium, or organic ammonium;

(II)

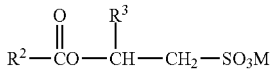

wherein $R^2$ represents an alkyl group having 4 or more and 22 or less carbon atoms; $R^3$ represents a hydrogen atom or an alkyl group having from 1 to 4 carbon atoms; and M represents a hydrogen atom, an alkali metal, an alkaline earth metal, ammonium, or organic ammonium;

(III)

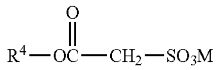

wherein $R^4$ represents an alkyl group having 4 or more and 22 or less carbon atoms, and M represents a hydrogen atom, an alkali metal, an alkaline earth metal, ammonium, or organic ammonium;

(IV)

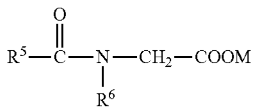

wherein $R^5$ represents an alkyl group having 8 or more and 22 or less carbon atoms; $R^6$ represents a hydrogen atom or an alkyl group having 1 to 4 carbon atoms; and M represents a hydrogen atom, an alkali metal, an alkaline earth metal, ammonium, or organic ammonium;

(V)

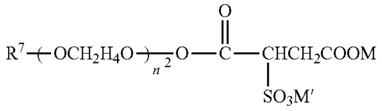

wherein $R^7$ represents an alkyl group having 8 or more and 22 or less carbon atoms; $n^2$ represents a number of 0 or more and 3 or less; and M and M' each independently represent a hydrogen atom, an alkali metal, an alkaline earth metal, ammonium, or organic ammonium; and $$R^8\text{—COOM} \quad \text{(VI)}$$

wherein $R^8$ represents an alkyl group having 8 or more and 22 or less carbon atoms; and M represents a hydrogen atom, an alkali metal, an alkaline earth metal, ammonium, or organic ammonium.

4. The method for washing hair of claim 3, wherein said component (B) is the anionic surfactant represented by Formulae (I):

$$R^1\text{—O—}(CH_2CH_2O)n^1\text{—}CH_2\text{—COOM} \quad \text{(I)}$$

wherein $R^1$ represents an alkyl group having 4 or more and 22 or less carbon atoms; $n^1$ represents a number of 4.0 or more and 16 or less; and M represents a hydrogen atom, an alkali metal, an alkaline earth metal, ammonium, or organic ammonium.

5. The method for washing hair according to claim 1, wherein a mass content ratio of the component (A) to the component (B) [component (A)/component (B)] is from 0.01 to 100.

6. The method for washing hair according to claim 1, wherein the number of carbon atoms in the internal olefin sulfonate (A) is 16 to 18.

7. The method for washing hair according to claim 1, wherein the internal olefin sulfonate (A) is obtained by sulfonating a raw material internal olefin having 16 to 18 carbon atoms, followed by neutralization and then hydrolysis.

8. The method for washing hair according to claim 1, wherein a total content of an internal olefin in which a double bond is present at a C-2 position in the raw material internal olefin is 5% to 20% by mass.

9. The method for washing hair according to claim 1, wherein the content mass ratio (the internal olefin sulfonate having 16 carbon atoms/the internal olefin sulfonate having 18 carbon atoms) is from 78/22 to 87/13.

* * * * *